United States Patent
Rosenberg et al.

(10) Patent No.: US 8,019,409 B2
(45) Date of Patent: Sep. 13, 2011

(54) CARDIAC RESYNCHRONIZATION THERAPY OPTIMIZATION USING ELECTROMECHANICAL DELAY FROM REALTIME ELECTRODE MOTION TRACKING

(75) Inventors: Stuart Rosenberg, Castaic, CA (US); Allen Keel, San Jose, CA (US); Kyungmoo Ryu, Palmdale, CA (US); Wenbo Hou, Lancaster, CA (US); Kjell Noren, Solna (SE); Thao Thu Nguyen, Bloomington, MN (US); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 392 days.

(21) Appl. No.: 12/416,771

(22) Filed: Apr. 1, 2009

(65) Prior Publication Data

US 2009/0306732 A1 Dec. 10, 2009

Related U.S. Application Data

(60) Provisional application No. 61/060,061, filed on Jun. 9, 2008.

(51) Int. Cl.
*A61B 5/04* (2006.01)
(52) U.S. Cl. .................................... 600/513
(58) Field of Classification Search ............. 600/513
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 5,297,549 A | 3/1994 | Beatty et al. | |
| 5,466,254 A | 11/1995 | Helland | |
| 5,476,483 A | 12/1995 | Bornzin et al. | |
| 5,553,611 A | 9/1996 | Budd et al. | |
| 6,240,307 B1 | 5/2001 | Beatty et al. | |
| 6,501,983 B1 * | 12/2002 | Natarajan et al. | 600/517 |
| 7,613,500 B2 | 11/2009 | Vass et al. | |
| 2005/0149138 A1 * | 7/2005 | Min et al. | 607/27 |
| 2006/0167529 A1 | 7/2006 | Schecter | |
| 2006/0178586 A1 | 8/2006 | Dobak, III | |
| 2007/0135721 A1 | 6/2007 | Zdeblick | |
| 2007/0167758 A1 | 7/2007 | Costello | |
| 2008/0058656 A1 | 3/2008 | Costello et al. | |
| 2008/0183072 A1 | 7/2008 | Robertson et al. | |
| 2008/0242976 A1 | 10/2008 | Robertson et al. | |
| 2009/0093857 A1 | 4/2009 | Markowitz et al. | |

FOREIGN PATENT DOCUMENTS

| | | | |
|---|---|---|---|
| WO | 2006042039 A2 | 4/2006 | |
| WO | 2006042039 A3 | 4/2006 | |
| WO | 2006105474 A2 | 10/2006 | |
| WO | 2006105474 A3 | 10/2006 | |
| WO | 2007111542 A1 | 10/2007 | |
| WO | 2007120290 A2 | 10/2007 | |
| WO | 2007120290 A3 | 10/2007 | |

* cited by examiner

*Primary Examiner* — George Manuel

(57) ABSTRACT

An exemplary method includes providing a mechanical activation time (MA time) for a myocardial location, the location defined at least in part by an electrode and the mechanical activation time determined at least in part by movement of the electrode; providing an electrical activation time (EA time) for the myocardial location; and determining an electromechanical delay (EMD) for the myocardial location based on the difference between the mechanical activation time (MA time) and the electrical activation time (EA time).

31 Claims, 13 Drawing Sheets

CARDIAC RESYNCHRONIZATION THERAPY OPTIMIZATION USING ELECTROMECHANICAL DELAY FROM REALTIME ELECTRODE MOTION TRACKING

CROSS REFERENCE TO RELATED APPLICATIONS

This application claims the benefit of U.S. Provisional Patent Application Ser. No. 61/060,061, filed Jun. 9, 2008, entitled "Cardiac Resynchronization Therapy Optimization Using Electromechanical Delay From Real-time Electrode Motion Tracking," and is related to U.S. patent application Ser. No. 11/676,108, filed Feb. 16, 2007, entitled "Motion-based Optimization of Cardiac Stimulation Therapy," both of which are incorporated by reference herein.

TECHNICAL FIELD

Subject matter presented herein relates generally to cardiac pacing and/or stimulation therapy. Various examples concern analysis of electromechanical information for optimizing such therapies, monitoring patient condition, monitoring device condition and the like.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dysynchrony is QRS width representative of contraction of both ventricles. For example, a QRS width greater than about 130 ms may indicate dysynchrony.

CRT can improve a variety of cardiac performance measures including left ventricular mechanical function, cardiac index, decreased pulmonary artery pressures, decrease in myocardial oxygen consumption, decrease in dynamic mitral regurgitation, increase in global ejection fraction, decrease in NYHA class, increased quality of life scores, increased distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Conventional placement criteria for a stimulation electrode typically focus on the location of latest electrical activation over the left ventricle. However, ischemic cardiomyopathy can cause non-uniform propagation of electrical activity over the myocardium. Thus, a site of latest electrical activation may not be optimal. In particular, such a site may be a poor candidate for maximizing cardiac stroke volume.

As described herein, various exemplary technologies allow a clinician, a system, etc., to optimize configuration of an implantable cardiac therapy device. In particular, various techniques include use of cardiac electrical information and cardiac mechanical information to determine one or more electromechanical delays, which can indicate better configurations and can improve diagnosis of cardiac conditions.

SUMMARY

An exemplary method includes providing a mechanical activation time (MA time) for a myocardial location, the location defined at least in part by an electrode and the mechanical activation time determined at least in part by movement of the electrode; providing an electrical activation time (EA time) for the myocardial location; determining an electromechanical delay (EMD) for the myocardial location based on the difference between the mechanical activation time (MA time) and the electrical activation time (EA time). Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
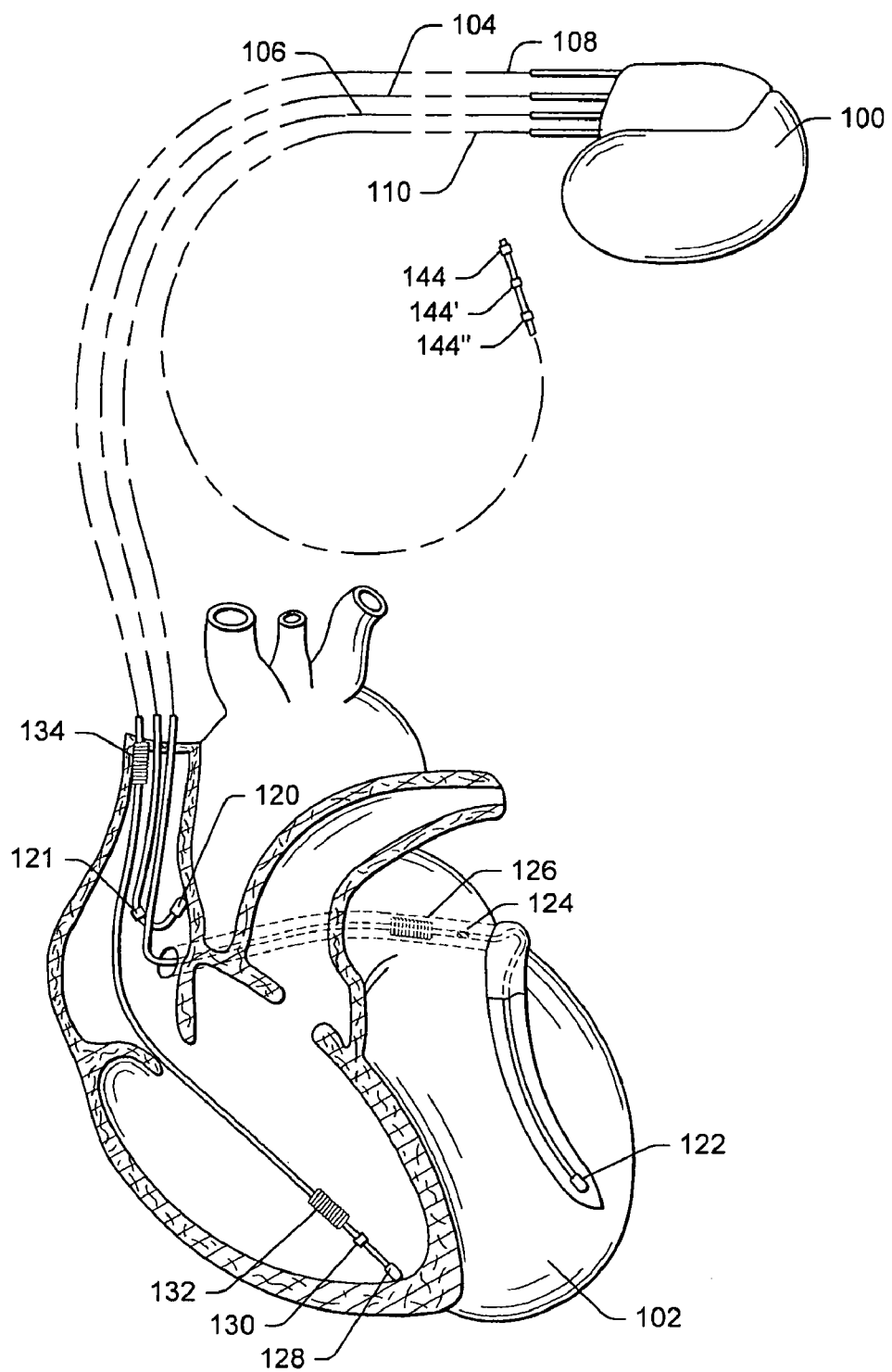
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations.

This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., rely on electrical information and mechanical information to optimize cardiac stimulation therapy, to monitor patient condition, to monitor implantable device condition, or to more fully understand cardiac health. As described herein, various techniques acquire information about cardiac electromechanics, e.g., electrical activity and mechanical activity. For example, an exemplary method includes positioning a plurality of electrodes in or on the heart, acquiring electrical information and acquiring mechanical information by tracking motion of the electrodes during at least part of a cardiac cycle. Such electrodes may be associated with a catheter for temporary placement, a lead for chronic implantation or a combination of both.

Position and motion tracking of an electrode or electrodes may be achieved in any of a variety of manners. For example, electrode patches may be placed on a patient's body to define a coordinate system (e.g., 1-D, 2-D, 3-D, etc.) and to aid in acquisition of position and motion information for one or more implanted electrodes (e.g., due to cardiac mechanics). An implanted electrode may be positioned via a vessel (e.g., a vein) or via the pericardium (e.g., intrapericardial access to an epicardial location). An implanted electrode may be used to deliver stimulation energy from a particular stimulation site and where multiple electrodes are implanted, various stimulation sites may be tested.

Electrical activity may be measured using conventional techniques such as those for acquiring surface electrocardiograms or in vivo electrocardiograms (e.g., intracardiac electrograms). As described herein, the term "electrogram" (EGM) includes surface electrogram (ECG) and intracardiac electrogram (IEGM) as well as other types of electrograms that rely on one or more implanted electrodes. Electrical information and mechanical information may be analyzed with respect to stimulation energy delivered using one or more stimulation sites. An analysis of such information may be used to determine an optimal stimulation site or sites or, more generally, an optimal configuration. As described herein, a "configuration" can account for more than electrode placement or location as one or more stimulation parameters and/or stimulation timings (e.g., interelectrode timings) may be part of a "configuration".

An exemplary stimulation device is described followed by various techniques for acquiring and analyzing electrical information and mechanical information. Data plots of electrical information and mechanical information from actual trials are shown and described with respect to various exemplary techniques. Exemplary methods and devices for real-time and post-processing techniques are also described. An exemplary program can optionally perform post-processing of information (e.g., electrical information and mechanical information) and be configured for programming an implantable device capable of delivering cardiac resynchronization therapy (CRT).

Exemplary Stimulation Device

The techniques described below are intended to be implemented in connection with any stimulation device that is configured or configurable to delivery cardiac therapy and/or sense information germane to cardiac therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
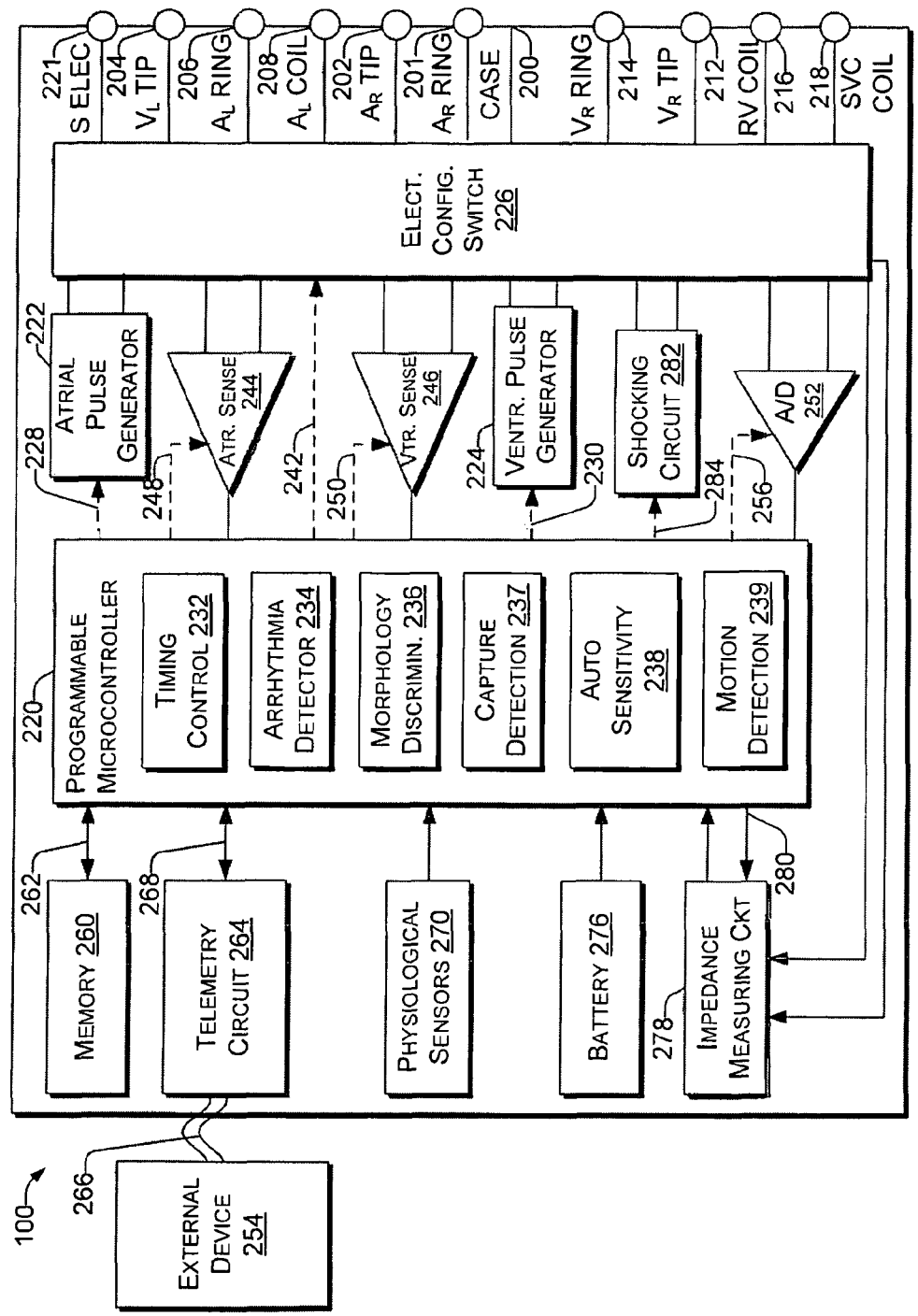
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional motion detection module 239. The module 239 may be used for purposes of acquiring motion information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor cardiac mechanics in relationship to cardiac electrical activity and may help to optimize cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
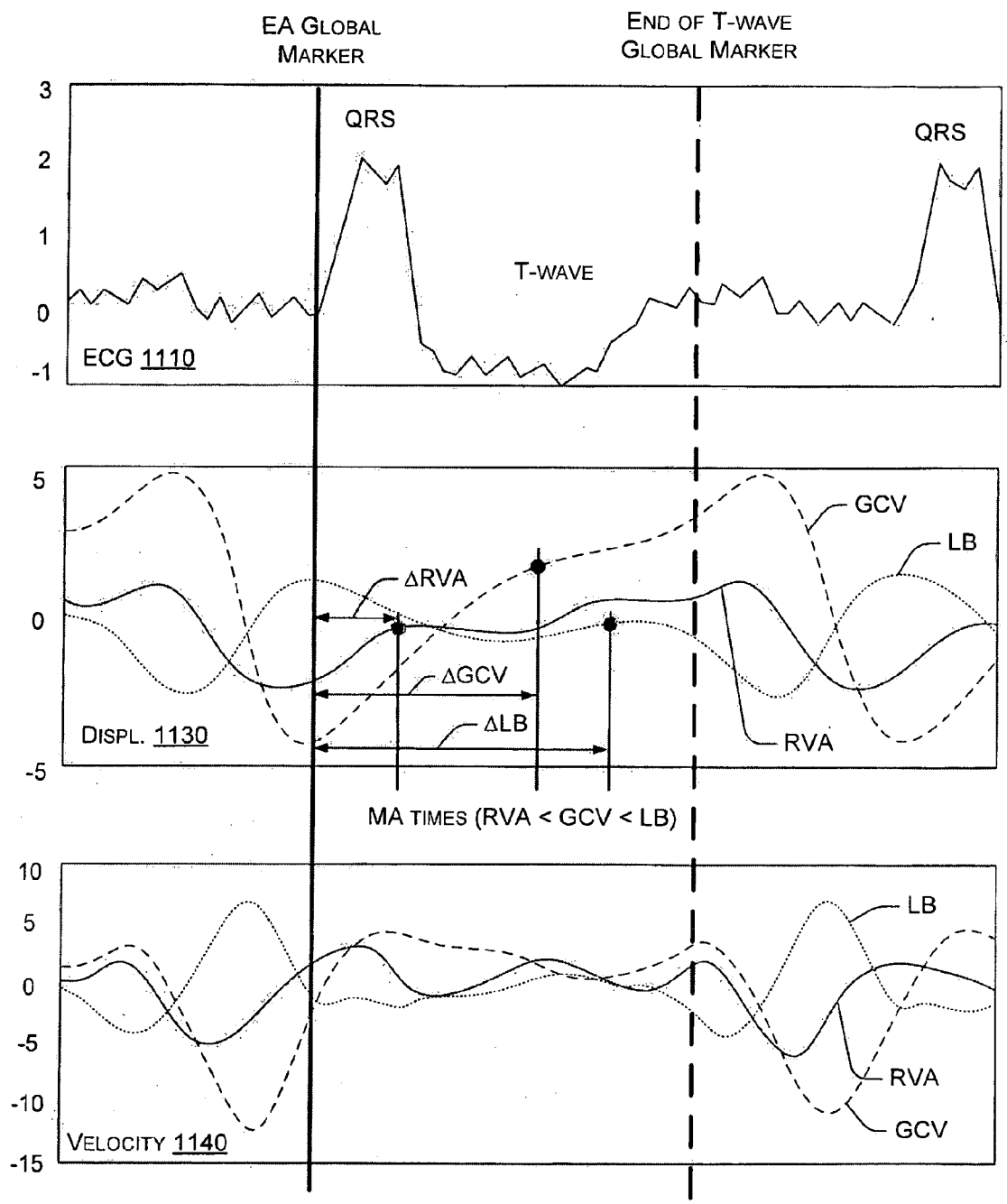
FIG. 11 is a series of plots for electromechanical information where markers indicate various aspects of mechanical activity (e.g., displacement).

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 cm²) and/or higher current frequencies (e.g., above about 10 kHz) to reduce noise.

Figure 3:
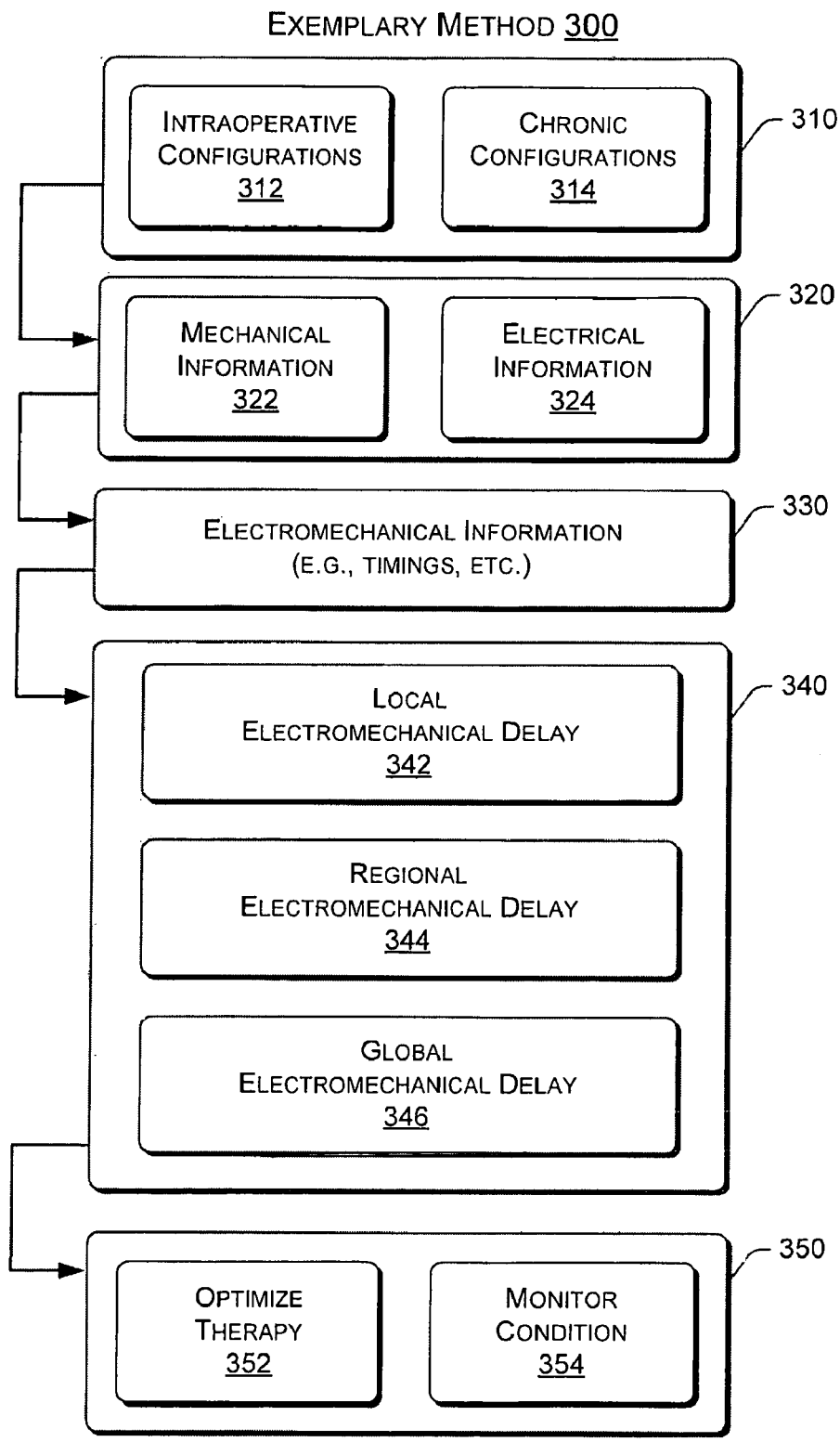
FIG. 3 is a block diagram of an exemplary method for optimizing therapy and/or monitoring conditions based at least in part on electromechanical information.

FIG. 3 shows an exemplary method 300 for acquiring and analyzing electromechanical information. In the example of FIG. 3, the method 300 includes a configurations block 310 that includes intraoperative configurations 312 and chronic configurations 314. The intraoperative configurations 312 pertain to configurations that may be achieved during an operative procedure. For example, during an operative procedure, one or more leads may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads. In general, intraoperative configurations include those achievable by re-positioning a lead in a patient's body while chronic configurations normally do not allow for re-positioning as a lead or leads are usually anchored during implantation or become anchored in the weeks to months after implantation.

As indicated in FIG. 3, an acquisition block 320 includes acquisition of mechanical information 322 and acquisition of electrical information 324. While an arrow indicates that a relationship or relationships may exist between the configurations block 310 and the acquisition block 320, acquisition of information may occur by using an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the heart; for acquisition of electrical information; for acquisition of mechanical information; for acquisition of electrical information and mechanical information; for delivery of energy to the heart and for acquisition of electrical information; for delivery of energy to the heart and for acquisition of mechanical information; for delivery of energy to the heart, for acquisition of electrical information and for acquisition of mechanical information.

In various examples, acquisition of mechanical information occurs by measuring one or more potentials where the measuring relies on an electrode that may also be configured to deliver energy to the heart (e.g., electrical energy to pace a chamber of the heart). In such a scenario, the electrode may deliver energy sufficient to stimulate the heart and then be tracked along one or more dimensions to monitor the mechanical consequences of the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to location and for acquiring an electrogram. To acquire potentials and an electrogram, circuitry may include gating or other sampling techniques. Such circuitry may rely on one sampling frequency for acquiring potentials for motion tracking and another sampling frequency for acquiring an electrogram.

Referring again to FIG. 3, an electromechanical information block 330 acts to combine the mechanical information 322 and the electrical information 324. In general, the mechanical information 322 and the electrical information 324 are acquired simultaneously or nearly simultaneously. For example, mechanical information and electrical information may be acquired for the same cardiac cycle. Or, alternatively, electrical information may be acquired during one cardiac cycle and mechanical information may be acquired during a next or subsequent cardiac cycle. In general, acquisition occurs such that the electromechanical information block 330 can associate the mechanical information 332 with the electrical information 334 (or vice versa). As described in more detail below, association of such information may be solely for the purpose of discerning timings of events (e.g., during a cardiac cycle). However, in other examples, rich data as to motion and electrical activity of the heart may be further analyzed.

The method 300 of FIG. 3 includes an electromechanical delay (EMD) block 340. The block 340 can determine local EMDs 342, regional EMDs 344, global EMDs 346 or other custom EMDs. For example, a local EMD 342 may be determined as the time between an electrical activation (e.g., intrinsic or delivered) and peak shortening or peak shortening velocity of a local region of the heart. A region EMD 344 may be determined based in part on information pertaining to one or more electrodes specified to represent motion of a region of the heart. A global EMD 346 may be determined as the time from a surface EGM Q-wave (or an atrial IEGM-far-field earliest deflection) to time of peak shortening velocity or to time of end systolic length where the number represents a global activation time. The method 300 may reach, in a conclusion block 350, a conclusion that the configuration yielding the shortest delay is the "optimal" configuration.

As shown in the example of FIG. 3, the conclusion block 350 may perform actions such as to optimize therapy 352 and/or to monitor patient and/or device condition 354. These options are described in more detail with respect to FIG. 4.

Figure 4:
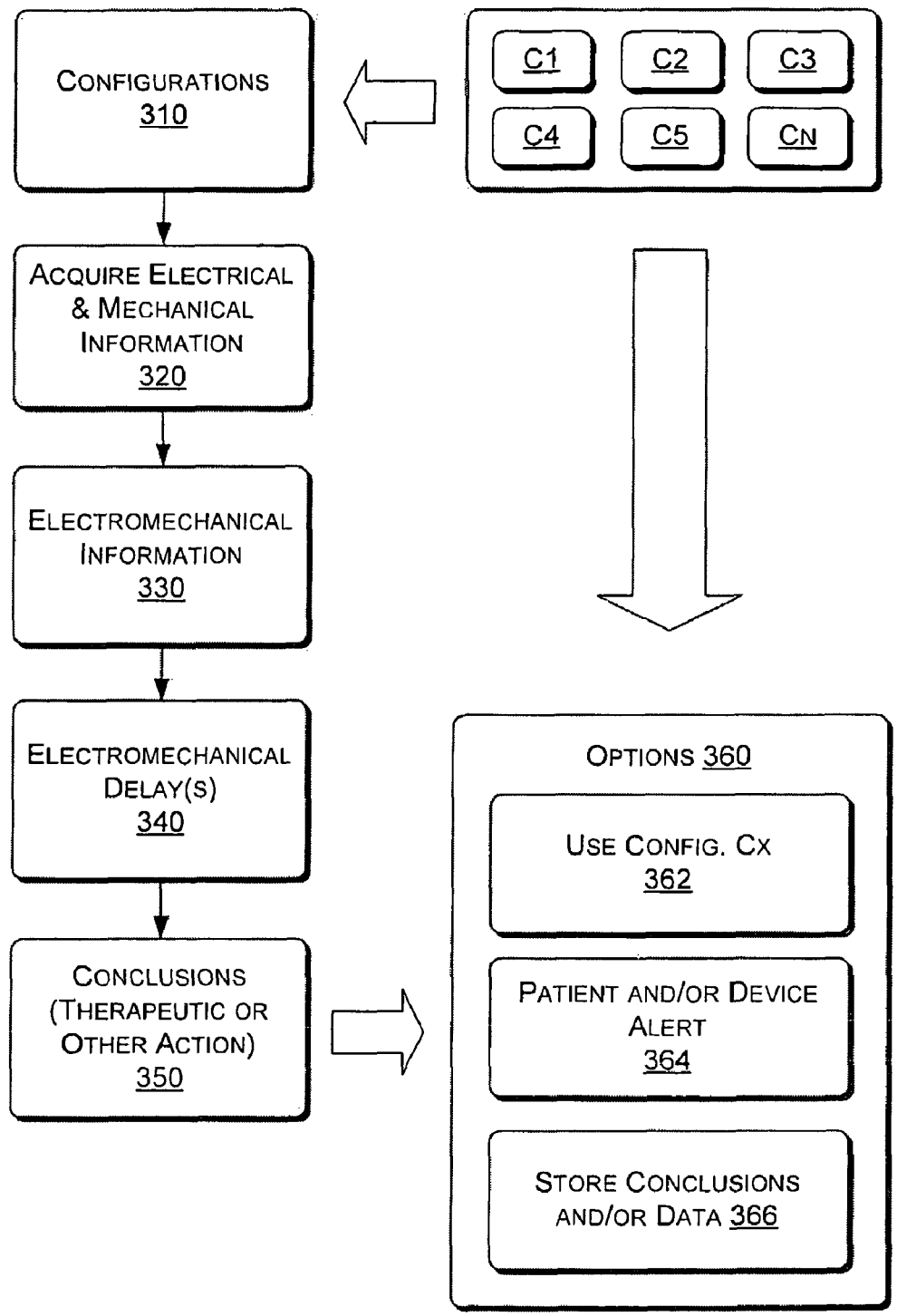
FIG. 4 is a block diagram of the exemplary method of FIG. 3 along with various options.

FIG. 4 shows the exemplary method 300 with various configurations 310 (C1, C2, . . . , Cn) and options 360. As mentioned, a configuration may be defined based on factors such as electrode position (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

In the acquisition block 320, acquisition occurs for electrical information and mechanical information where such information pertains to one or more configurations. In the electromechanical information block 330, the electrical information and the mechanical information are associated, for example, to provide timings. In the electromechanical delay(s) block 340, one or more electromechanical delays are determined based at least in part on the electromechanical information (e.g., timings used to determine delays). The conclusions block 350 provides for therapeutic or other action, which may be selected from one or more options 360. In the example of FIG. 4, the one or more options 360 include selection of a configuration 362 (e.g., Cx, where x is a number selected from 1 to n), issuance of a patient and/or device alert 364 that pertains to condition of a patient or a condition of a device or associated lead(s) or electrode(s), and storage of conclusion(s) and/or data 366. The options 360 may be associated with the configurations 310, as indicated by an arrow. For example, storage of conclusions and/or data 366 may also store specific configurations, a generalization of the configurations (e.g., one or more shared characteristics), a device/system arrangement (e.g., where the number and types of configurations would be known based on the arrangement), etc.

As described herein, an exemplary method can include: positioning one or more electrodes within the heart and/or surrounding space (e.g., intra-chamber, intra-vascular, intra-pericardial, etc., which may be collectively referred to as "cardiac space"); acquiring mechanical information (e.g., via one or more measured potentials) to determine a location, locations or displacement for at least one of the one or more electrodes using an electroanatomic mapping system (e.g., the ENSITE® NavX system or other system with appropriate features); and acquiring electrical information (e.g., one or more intracardiac electrograms) using one or more of electrodes and an implantable device or an external device coupled to the electrodes. In such a method, the positioned electrodes may be configured for acquisition of electrical information. Further, with respect to acquisition of information, acquisition systems may operate at appropriate sampling rates. For example, an acquisition system for mechanical information may operate at a sampling rate of about 100 Hz (e.g., the ENSITE® NavX system can sample at about 93 Hz) and an acquisition system for electrical information may operate at a sampling rate of about 1200 Hz (e.g., in unipolar, bipolar or other polar arrangement).

As explained, the mechanical information and the electrical information may be combined to determine timings or values. In turn, electromechanical delays (EMDs) may be determined and used to select or optimize therapy or for one or more other purposes.

An exemplary method may include preparing a patient for both implant of a device such as the device 100 of FIGS. 1 and 2 and for electroanatomic mapping study. Such preparation may occur in a relatively standard manner for implant prep, and using the ENSITE® NavX system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a CRT system, as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or locating system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay). Simultaneous to the position recording, an intracardiac electrogram from each electrode can also be recorded and associated with the anatomic position of the electrode. While various examples refer to simultaneous acquisition, acquisition of electrical information and acquisition of mechanical information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time motion information at each electrode position in a point-by-point manner. Such motion data can by associated with a respective anatomic point from which it was collected. By moving the electrodes from point to point during an intervention, the motion data from each location can be incorporated into a single map, model, or parameter.

As explained, an exemplary method may include determining one or more of the electromechanical delays. In turn, an algorithm or a clinician may select a configuration (e.g., electrode location, multisite arrangement, AV/VV timing) that yielded the best value for an electromechanical delay parameter and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single parameter or a combination of more than one parameter, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.).

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization of a chronically implanted system, in general, electrode location will not be altered, but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics while one or more electrodes for measuring potential may be placed at a location or locations that vary with respect to cardiac mechanics. Alternatively, electrodes for measuring potential may be placed at locations that do not vary significantly with respect to cardiac mechanics while one or more electrodes for delivery of current may be placed at a location or locations that vary with respect to cardiac mechanics. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

Figure 5:
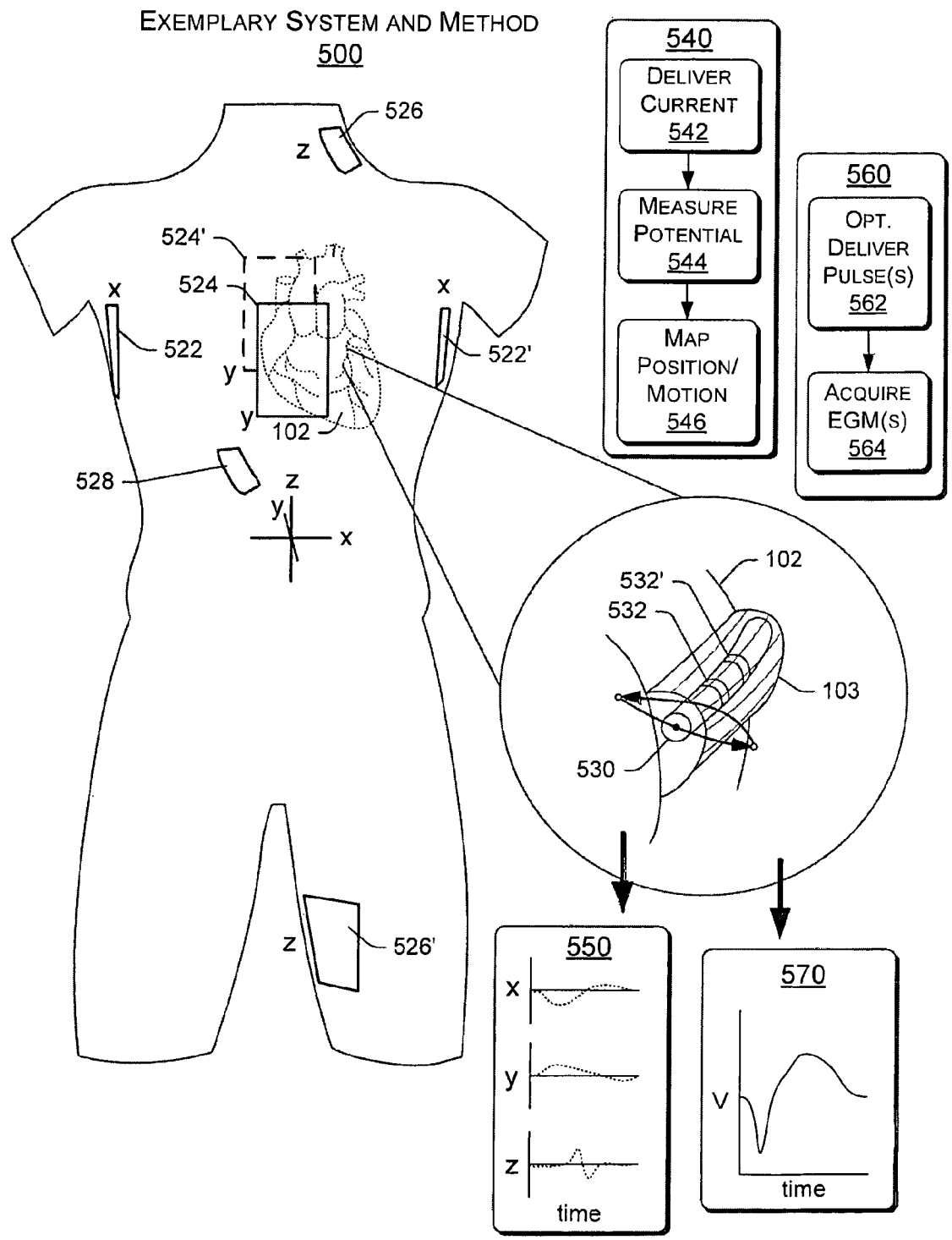
FIG. 5 is an exemplary arrangement of a lead and electrodes for acquiring electrical information and mechanical information with respect to time.

FIG. 5 shows an arrangement and method 500 that may rely in part on a commercially available system marketed as ENSITE® NavX navigation and visualization system (see also LocaLisa system). The ENSITE® NavX system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis), 524, 524' (y-axis) and 526, 526' (z-axis). An addition electrode patch 528 is available for reference, grounding or other function. The ENSITE® NavX System can also collect electrical data from a catheter and can plot a cardiac electrogram 570 from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NavX system may use electrical information to track or navigate movement and construct three-dimensional (3-D) models of a chamber of the heart.

A clinician can use the ENSITE® NavX system to create a 3-D model of a chamber in the heart for purposes of treating arrhythmia (e.g., treatment via tissue ablation). To create the 3-D model, the clinician applies surface patches to the body. The ENSITE® NavX system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NavX system) delivers low level separable currents from the three substantially orthogonal electrode pairs (522, 522', 524, 524', 526, 526') positioned on the body surface (delivery block 542). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion mapping block 546). Where the catheter (or lead) 530 moves, the method 540 may also measure motion.

In addition to mapping at specific points, the ENSITE® NavX system provides for interpolation (mapping a smooth surface) onto which activation voltages and times can be registered. Around 50 points are required to establish a surface geometry and activation of a chamber at an appropriate resolution. The ENSITE® NavX system also permits the simultaneous display of multiple catheter electrode sites, and also reflects real-time motion of both ablation catheters and those positioned elsewhere in the heart.

The ENSITE® NavX system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion, the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the mapping block 546 to map motion based at least in part on the measured potential. According to such a method, motion during systole and/or diastole may be associated with electrical information. Alone, or in combination with electrical information, the mechanical motion information may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NavX system. For example, one or more pairs of electrodes (522, 522', 524, 524', 526, 526') may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track motion of one or more electrodes due to systolic motion, diastolic motion, respiratory motion, etc. Electrodes may be positioned along the endocardium and/or epicardium during a scouting or mapping process for use in conjunction with electrical information. Such information may also be used alone, or in conjunction with electrical information, for identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and motion information may be acquired where the motion information is associated with the controlled cardiac mechanics. An exemplary selection process may identify the best stimulation site based on factors such as electrical activity, electromechanical delay, extent of motion, synchronicity of motion where motion may be classified as systolic motion or diastolic motion. In general, motion information corresponds to motion of an electrode or electrodes (e.g., endocardial electrodes, epicardial electrodes, etc.) and may be related to motion of the heart.

Figure 6:
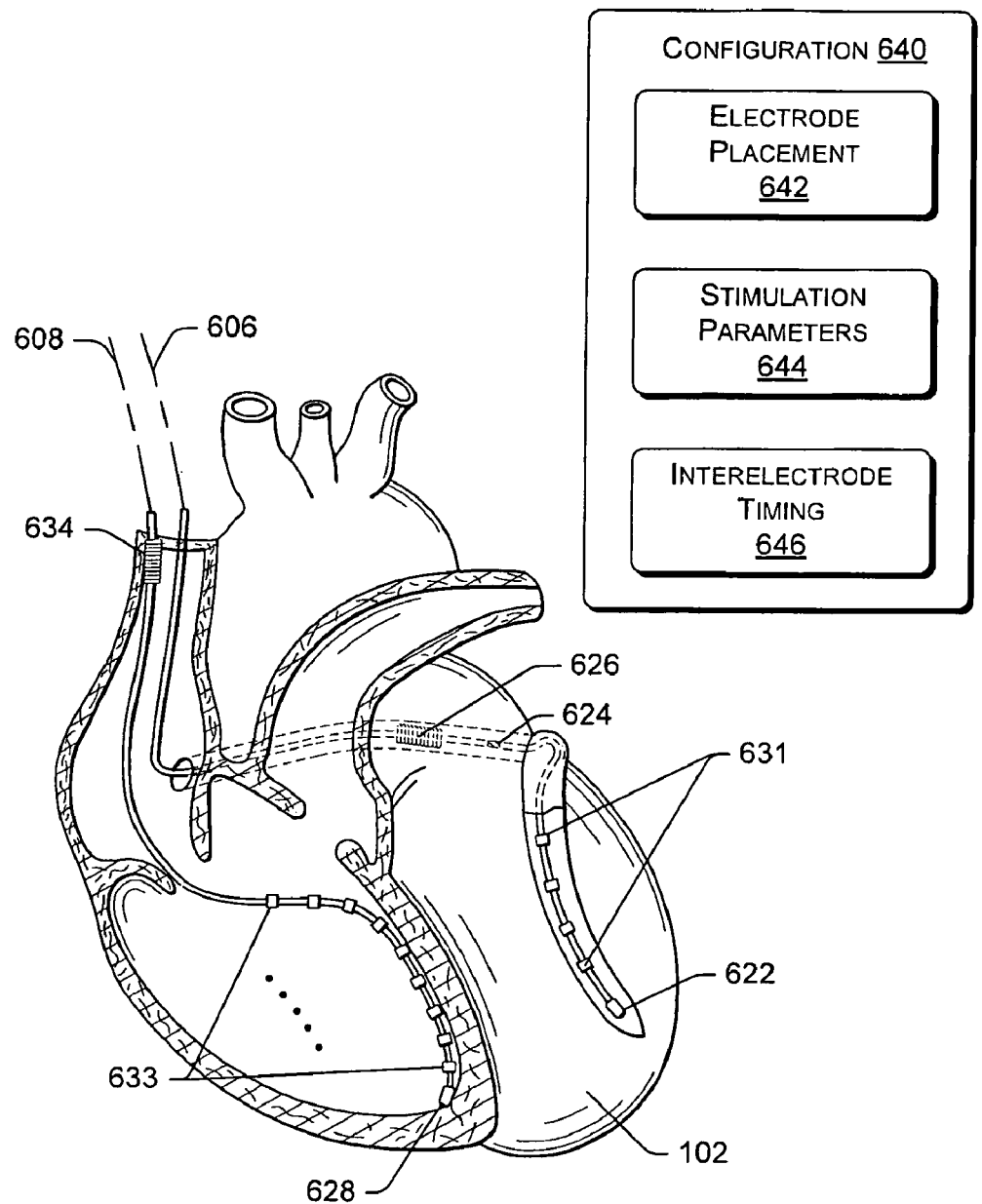
FIG. 6 is a simplified diagram illustrating an exemplary arrangement that includes at least one multipolar lead positioned in a chamber of the heart and associated factors to define a configuration.

FIG. 6 shows an exemplary arrangement 600 that includes a multipolar lead 608 positioned in the right ventricle and another multipolar lead 606 positioned in the coronary sinus and a vein of the left ventricle. Also shown is a block 640 of exemplary configuration parameters. In the arrangement 600, the lead 608 includes a tip electrode 628, a series of ring electrodes 633 and a coil electrode 634. The lead 606 includes a tip electrode 622, a series of ring electrodes 631, another ring electrode 624 and a coil electrode 626. In the example of FIG. 6, the lead 608 extends from the SVC through the right atrium and into the right ventricle. The tip electrode 628 is positioned near the apex of the heart 102, which is typically a region that moves less than other regions during contraction. At least some electrodes of the series of ring electrodes 633 are positioned along the septal wall (septal wall between the right ventricle and the left ventricle). As shown, the lead 606 enters the right atrium via the SVC and passes through the ostium of the coronary sinus to the coronary sinus and into a contributory vein thereof. In the example of FIG. 6, the contributory vein runs along a wall of the left ventricle and the series of ring electrodes are thereby positioned along the wall. In the arrangement 600, movement of the septal wall and a lateral LV wall may be tracked using one or more of the electrodes 633 and one or more of the electrodes 631.

Where a coronary sinus lead includes a bifurcation, then electrodes may be optionally positioned in more than one contributory vein. In yet other examples, a basket type lead may be used with spines that may extend to an interior wall of chamber of the heart. Such spines may include one or more electrodes for use in acquiring cardiac motion information.

The electrodes 631 and 633 may be used according to the exemplary methods 540 and/or 560 of FIG. 5. For example, in the delivery block 542, current may be delivered to a region of the heart that includes at least some of the series of electrodes 631 and/or 633. In the measurement block 544, one or more of the series of electrodes 631 and/or 633 may be used to measure potential or potentials. Such potential or potentials may be measured at a particular point in time or at more than one point in time. The mapping block 546 can then use the potential or potentials to map motion of the right ventricle (e.g., the septal wall) and to map motion of the left ventricle (e.g., the lateral wall).

With respect to delivery of current per the delivery block 542, surface patches may be used (e.g., 522, 522', 524, 524', 526, 526' of FIG. 5) or, for example, one or more implanted electrodes (e.g., electrodes of FIG. 1). Where implanted electrodes are used, for example, a lead and can arrangement may deliver current (e.g., per block 542) and while another lead measures potential (e.g., per block 544). Hence, one or both leads 606 and 608 may be configured for measurement of potential and for delivery of current.

With respect to the method 560, one or more EGMs may be acquired per an acquisition block 564. The method 560 also includes an optional delivery block 562. Where the delivery block 562 is implemented, the acquisition block 564 may acquire one or more EGMs in response to delivery of a stimulus or stimuli. As mentioned, the method 560 allows for acquisition of electrical information, which may be used in conjunction with the mechanical information.

In various examples, electrical information may be used to trigger acquisition of mechanical information. For example, delivery of a stimulus and/or detection of a feature in an EGM may trigger acquisition of mechanical information (e.g., motion tracking of an electrode or electrodes). Such a trigger may occur in real-time (e.g., for the same cardiac cycle) or a trigger may occur in a subsequent cardiac cycle based at least in part on a previously detected EGM feature. For example, during a cardiac cycle, an EGM may be acquired, a feature detected and a time assigned to the feature and then in a subsequent cardiac cycle (e.g., a next cycle) the time may be used to trigger motion tracking (e.g., by triggering measurement of one or more potentials during delivery of locating current). In such an example, a number of EGMs may be analyzed and averaged to more accurately determine a trigger time for triggering motion tracking (or simply measurement of one or more positions at a point in time).

As already described, various exemplary techniques may be used to acquire motion information (e.g., spatially for 1-D, 2-D or 3-D and generally with respect to time). In general, acquisition of motion information relies on current delivery and potential measurement. Electrodes may be positioned in the body and/or external to the body. Electrodes may be positioned within the pericardial space, as defined by the pericardium (e.g., in a vessel/chamber of the heart, etc.), and/or outside the pericardial space (e.g., consider the case electrode of the device 100 of FIGS. 1 and 2 or the surface patch electrodes of the system 500 of FIG. 5). Electrodes may be positioned at the pericardium, at the epicardial surface of the heart or between the pericardium and the epicardial surface of the heart. Electrodes may be implanted chronically or temporarily. Electrodes may optionally be suitable for stimulating the heart (e.g., pacing, shocking, etc.).

With respect to the configuration block 640 of FIG. 6, as mentioned, a configuration may be defined based on factors such as electrode placement 642, stimulation parameters 644 and interelectrode timing 646 as well as one or more other factors, as appropriate. In various examples, a configuration includes at least one electrode in the right ventricle (preferably both tip and ring of the RV pacing or defibrillation lead); and at least one electrode in the left ventricle (preferably tip both tip and ring of a coronary sinus pacing lead). As shown in FIG. 1, other electrodes may include the tip electrode 120 and the ring of the right atrial lead 104. As shown in FIG. 6, a plurality of electrodes on a multipolar lead 606 and 608 may be used. Or, as mentioned, a multipolar EP catheter or a multipolar introducer catheter (e.g., in the coronary sinus, a branch of the coronary sinus, etc.) may be used.

As explained with respect to FIGS. 3, 4 and 5, an exemplary method may acquire a variety of information pertaining to location or movement of an electrode (e.g., that may move as part of the heart moves or remain stationary as a fiducial marker) and electrical activity of the heart (e.g., IEGM, surface ECG, other). In various methods, location and EGM signals from one or more electrodes are recorded over time. Such a method may record information for each possible configuration or for a select set of configurations. Such a method may also record surface ECG and possibly other biological signals such as impedance, pressure, respiration, etc.

By providing a set of configurations and underlying defining factors, an algorithm can then vary one or more of the factors to progressively select each configuration of the set. For example, an algorithm may vary one or more of: pacing lead positions (e.g. RV apex or RV septum, CS lateral branch distal or proximal, or CS anterior branch, etc.); a set or subset of pacing electrodes on a single lead or across various leads; PV, AV or VV timing; programmed sequential stimulation; electrode polarity; stimulus voltage; current or pulse width; and/or other parameters. Information acquired can be processed for each configuration and results for each configuration may be stored and then compared across multiple configurations. An exemplary method may include selecting a configuration with the best result, which can then be implemented to optimize deliver of a cardiac pacing therapy such as CRT.

An exemplary method includes positioning an implantable lead in a chamber of the heart where the lead includes a series of electrodes and where at least some of the electrodes contact an interior wall of the chamber, delivering current, measuring potentials, associated with the current, using the electrodes that contact the interior wall of the chamber and mapping motion of the interior wall based at least in part on the measured potentials. Such a method may include delivering current using one or more electrodes positioned on the skin of the patient and/or one or more implanted electrodes. Such a method may deliver current to generate at least a one-dimensional coordinate system. In the foregoing method, the interior wall may be the septal wall between the right ventricle and the left ventricle or it may be a free wall of the right ventricle or a free wall of the left ventricle. Mapped motion of a chamber wall may be considered mechanical information and such information may be associated with electrical information, for example, to determine one or more electromechanical delays (EMDs). As described herein, EMDs may be used for selecting one or more parameters of a bi-ventricular pacing therapy.

Figure 7:
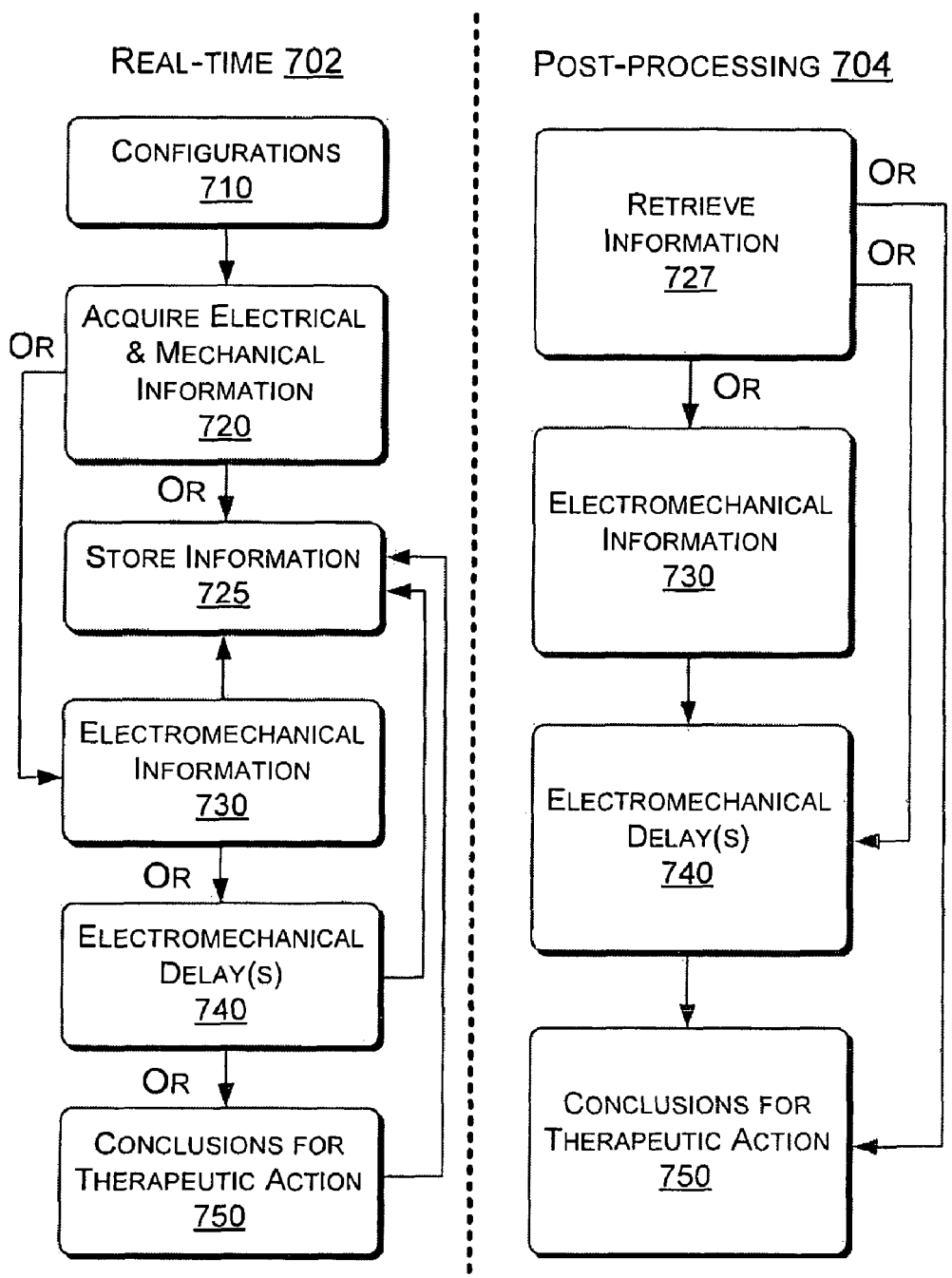
FIG. 7 is a block diagram of an exemplary method that includes real-time steps and optionally post-processing steps.

FIG. 7 shows an exemplary method 700 that can include real-time processing 702 and post-processing 704. The method 700 provides for an explanation of intraoperative performance (e.g., during exploration of patient condition and/or during implantation of an implantable device) and chronic performance (e.g., after implantation of an implantable device).

The real-time processing 702 includes a configurations block 710 and an acquisition block 720 (see, e.g., the method 300 of FIGS. 3 and 4). In the example of FIG. 7, the real-time processing 702 also includes a storage block 725 where information may be stored and later retrieved by a retrieval block 727 as part of the post-processing 704. The real-time processing 702 optionally includes an electromechanical information block 730, an electromechanical delay block 740 and/or a conclusions block 750 (e.g., as explained with respect to the method 300 of FIGS. 3 and 4).

In FIG. 7, various arrows indicate possible flow paths for the method 700. For example, the storage block 725 may store acquired information per the acquisition block 720, store electromechanical information per the block 730, store one or more electromechanical delays per the block 740 and/or store conclusions for therapeutic action or diagnoses per the block 750.

The retrieval block 727 of the post-processing 704 may retrieve any of a variety of stored information stored per the storage block 725. The post-processing 704 may perform actions such as associating mechanical information and electrical information per the block 730, determining one or more electromechanical delays per the block 740 and/or making one or more conclusions per the block 750.

As described herein, an exemplary intraoperative system can perform in real-time or near real-time as indicated by the real-time processing 702 of FIG. 2 as well as the methods 300 of FIGS. 3 and 4. So-called real-time or near real-time provide for presentation of results and decisions to be made during an operative procedure. For example, during an operative procedure, a clinician may select a configuration by positioning a catheter or lead, acquire electrical information and mechanical information, associate the information, determine one or more electromechanical delays and consider results (e.g., visually on a screen, audibly or tactilely) to thereby assist the operative procedure. For example, in response to results, a clinician may select a different configuration and repeat the real-time process. A clinician may alternatively or additionally decide that a patient is or is not a candidate for a particular therapy (e.g., likely to be a responder to CRT or not a responder to CRT).

After implantation of an implantable device, a clinician may follow the post-processing 704 of FIG. 7. For example, an implantable device (see, e.g., the device 100 of FIGS. 1 and 2) may be programmed to perform actions of blocks 720 and 725. During a follow-up consultation for a patient, a clinician may retrieve stored information (e.g., per block 727) by interrogating the implantable device and/or accessing a database that includes information stored per the storage block 725. Interrogation of an implantable device may occur locally (e.g., in-person) or remotely (e.g., using a device local to the patient that can transmit information retrieved from the patient's implantable device). In this example, the clinician would perform post-processing 704 actions of blocks 730, 740 and 750. As indicated by the arrows, other paths exist. For example, an implantable device may be configured to associate electrical information and mechanical information per block 730 and/or be configured to determine one or more electromechanical delays per block 740. In such instances, the retrieval block 727 may retrieve processed data stored by the storage block 725.

Figure 8:
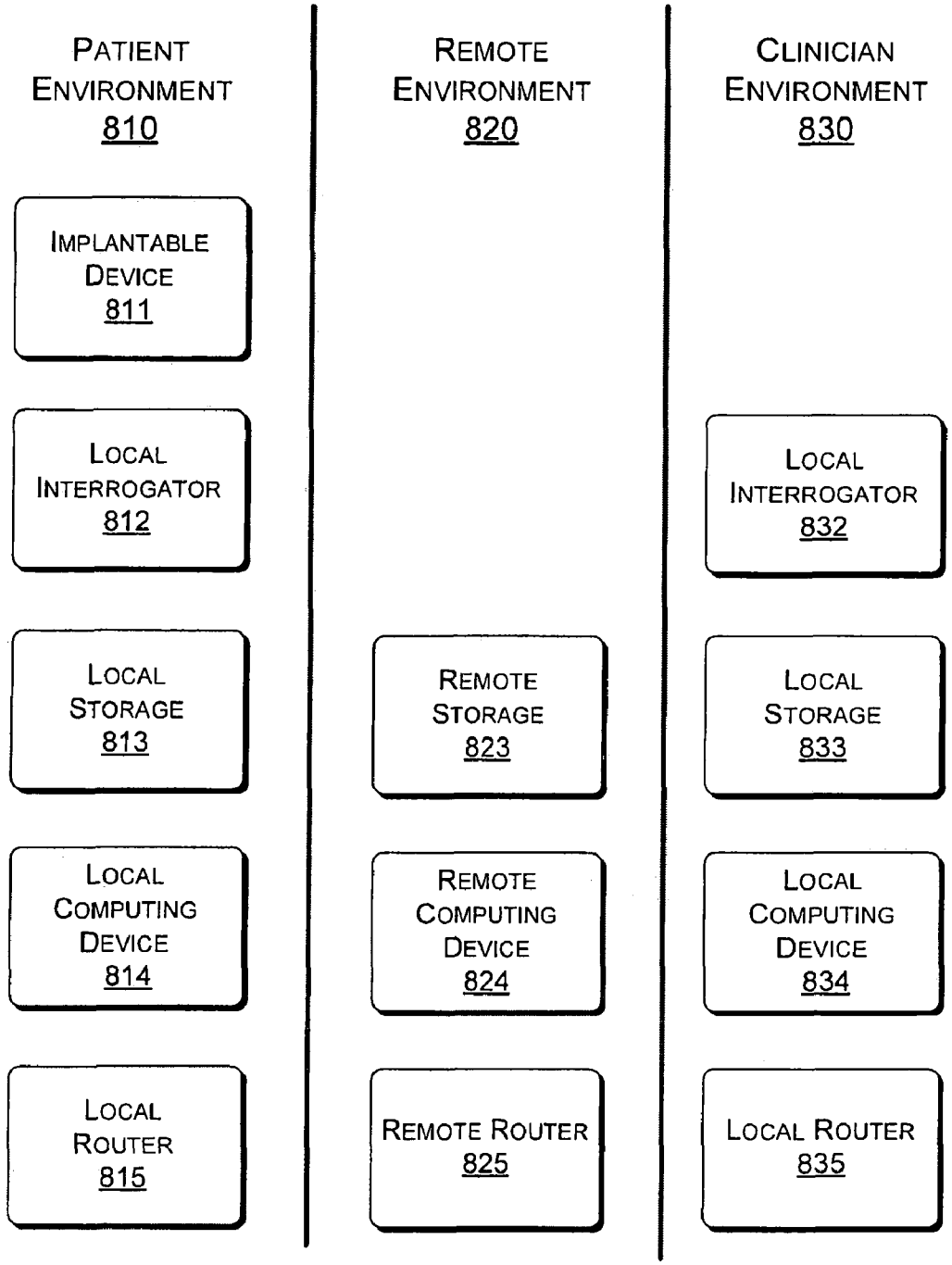
FIG. 8 is a block diagram of components in various environments that help to illustrate exemplary schemes.

Various scenarios exist where tasks of storage, retrieval and computation (e.g., data processing) may be distributed amongst two or more devices. FIG. 8 shows exemplary schemes 800 that includes a patient environment 810, a remote environment 820 and a clinician environment 830. A patient in the patient environment 810 includes an implantable device 811, which provides for acquisition of mechanical information and electrical information. While not shown in FIG. 8, other equipment such as a surface ECG, a location system, etc., may be in the patient environment 810 or the clinician environment 830 to acquire information.

The patient environment 810 may include one or more of a local interrogator 812, a local storage 813, a local computing device 814 and a local router 815. A local interrogator 812 may be a device such as the in-home device of the HOUSECALL® system marketed by St. Jude Medical (Sylmar, Calif.). Such a device allows clinicians to provide patients with a convenient and comprehensive alternative to in-office visits. Patient data reports are triaged and can be accessed via the Internet, faxed, or uploaded to an office networking system. Unlike remote implantable cardiac defibrillation (ICD) monitoring systems that store only limited data for review later, the HOUSECALL PLUS® system can provide a live medical professional to analyze the transmissions immediately and communicate with the patient. Calls can be initiated by the patient or follow-up center, and the system can be owned and operated by the office, clinic, or hospital.

The HOUSECALL PLUS® system makes it possible to monitor parameters and settings on an ICD, clear diagnostics and evaluate the following: real-time electrograms, surface ECGs, delivered therapies and stored electrograms. Such a system allows for availability of complete diagnostics, for example, equivalent to a full, in-office programmer-based interrogation. Such a system can minimize follow-up visits, indicate when a patient should be seen, and help avoid unwarranted trips to the emergency room.

The local storage 813 may be part of or in communication with the interrogator device 812. Similarly, the local computing device 814 may be part of or in communication with the interrogator device 812. With respect to the local router 815, this may be a device to assist in communications. For example, the implantable device 811 and/or the interrogator device 812 may include communication circuitry according to a wireless standard (e.g., WiFi or Bluetooth) and the router 815 may act to direct wireless communications between devices where one or more of the devices may further connect with the Internet or other network.

The remote environment 820 of FIG. 8 represents an intermediate environment where information can be received, relayed, stored, processed, etc. For example, the remote storage 823 may store information retrieved from many implantable devices (e.g., directly or indirectly). A remote computing device 824 may be a server for controlling the remote storage 823 and/or for processing information. A remote router 825 may route communications and associated information from one point to another with or without any actions by the remote storage 823 and/or with or without any actions by the remote computing device 824.

The clinician environment 830 includes a local interrogator 832, a local storage 833, a local computing device 834 and a local router 835. This equipment may function to allow a clinician to perform real-time processing 702 and/or post-processing 704, as explained with respect to FIG. 7. As mentioned, a clinical or clinician environment may include various other equipment (e.g., echocardiogram, ECG, stress test equipment, biological sensors, etc.).

The clinician environment 830 of FIG. 8 may be an environment suited for catheterization, device implantation, etc. Where a method that analyzes electromechanical information is performed in such an environment, the components 832, 833, 834 and 835 (and/or other components) may be used intraoperatively. As explained in an intraoperative environment, real-time analysis is desirable. However, since an optimization process may be iterative or may be involve choosing the best of a number of attempted configurations, a fast post-processing scheme still allows intraoperative utilization of the techniques described here.

Where the clinician environment 830 of FIG. 8 is an environment for follow-up consultation, real-time processing requirements may not be as pressing and a post-processing computation scheme may be acceptable.

FIGS. 9, 10, 11 and 12 show various plots of trial data acquired using a canine model. Various exemplary data analysis techniques are described with respect to the plotted data, which may be implemented according to various exemplary methods (e.g., the method 300 of FIGS. 3 and 4 and the method 700 of FIG. 7).

Figure 9:
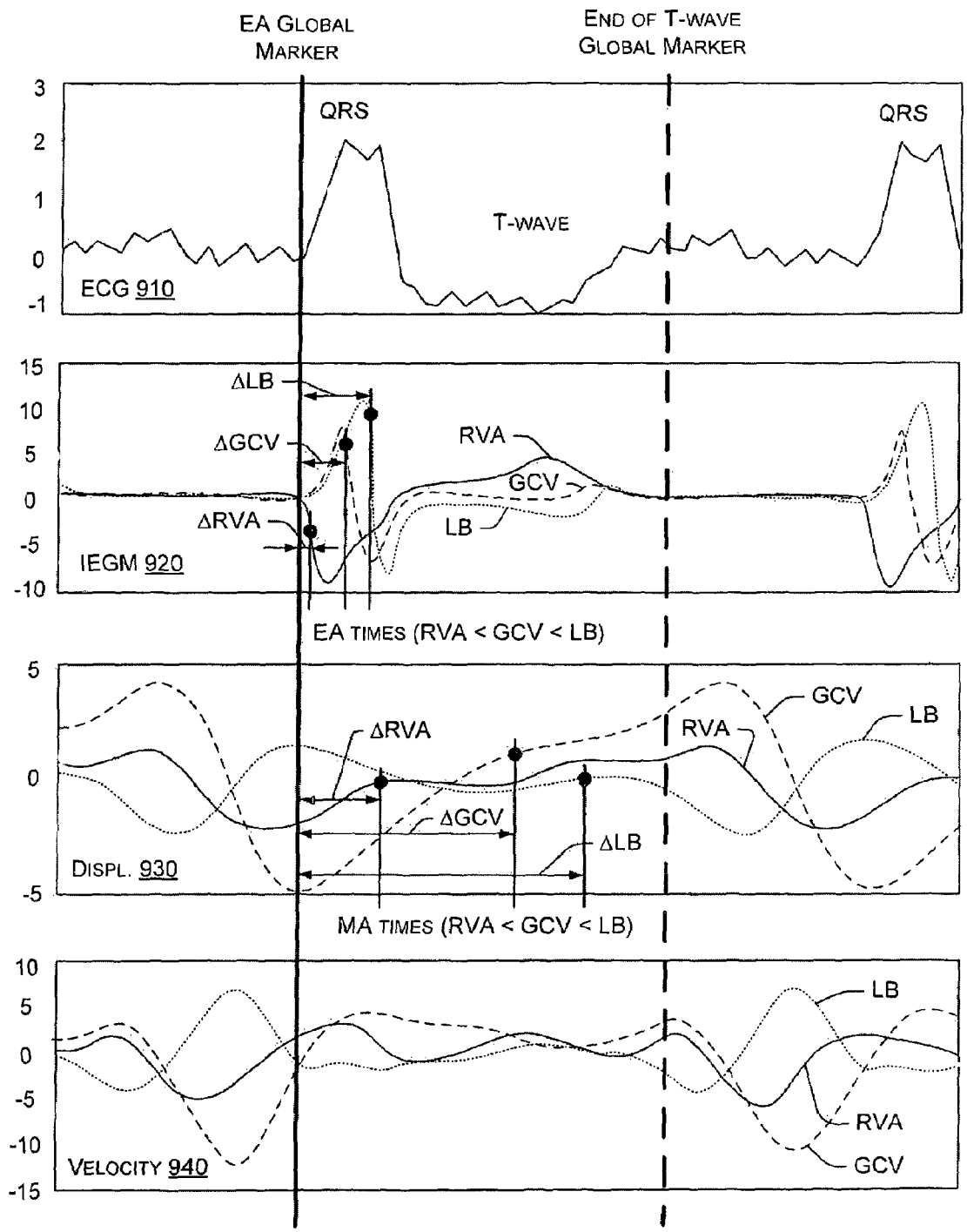
FIG. 9 is a series of plots for electromechanical information where markers indicate various aspects of electrical activity (e.g., IEGM) and mechanical activity (e.g., displacement).

FIG. 9 shows a series of plots including an ECG plot 910, an IEGM plot 920, a displacement plot 930 and a velocity plot 940. The trial data of FIG. 9 was acquired based on spontaneous rhythms (e.g., intrinsic). Arrangements included electrode-bearing leads positioned in the RV apex (RVA, solid curve), Great Cardiac Vein (GCV, dashed curve), and Lateral Branch (LB, dotted curve). The ECG plot 910 data was acquired using surface electrodes and the IEGM plot 920 data was acquired using unipolar sensing. Data in the plots 930 and 940 is discussed further below.

A solid black vertical line extends across all of the plots and represents a time marker for the end diastole, or onset of a global QRS complex (e.g., a global electrical activation time marker). A dashed black vertical line extends across all of the plots and represents a global time marker for the end of the T-wave, which occurs after the end of systole during repolarization.

As described herein, a local electrical delay can be identified based on the "global" ECG data and the various "local" IEGM data (electrical information), for example, from onset of the ECG QRS complex to onset of individual local electrical activation as determined by steepest descent of IEGM data acquired for the RVA, GCV and LB. These points in time (electrical activation times) are marked with vertical lines where the local electrical delays are indicated by ΔRVA, ΔGCV and ΔLB as being the measured from the "global" end diastole time to an activation feature of a respective IEGM (e.g., based on steepest or other feature).

As described herein, local mechanical activation is found from peak systolic displacement, which may be defined as the peak of the displacement curve or alternatively as a threshold amplitude, i.e., an inflection point of the displacement curve between onset of a Q-wave to the end of a T-wave. In the displacement plot 930 of FIG. 9 (mechanical information), the mechanical activation times for the RVA, GCV and LB correspond to inflection points (filled circles) and are indicated with vertical lines (MA times).

As shown in FIG. 9, the global QRS complex time from the surface ECG data (plot 910) can be used to associate the local electrical information (IEGMs of the plot 920) and the local mechanical information (displacement data of the plot 930). As mentioned, such association allows for determination of local electromechanical delays as it can provide a common timeline for electrical events and mechanical events. Where a common timeline exists, inherently or by other means, then an association exists upon acquisition of the electrical information and the mechanical information.

For purposes of determination of local electromechanical delays (LEMDs), at each electrode, the time of electrical activation can be determined from "local" EGM data (e.g., detection by peak amplitude, peak negative slope, achieving a threshold voltage or slope, etc.). The electrode position $\vec{x}_0$ at the time of electrical activation can be noted for one or more electrodes. The electrode position $\vec{x}_0$ at each subsequent time sample (e.g., until the time of the next detected electrical activation) can be noted, and a distance vector computed as the vector difference between the current position and the position at activation $\vec{s}_i = \vec{x}_i - \vec{x}_0$.

As shown in FIG. 9, mechanical activation can be determined as a point of inflection on an upward trending portion of a displacement curve over all points i in a global time window, e.g., time between onset of a Q-wave to the end of a T-wave. For example, mechanical activation may correspond to a point in the displacement curve where increases in consecutive, adjacent or nearby samples $S_i = |S_i|$ become increasingly smaller so as to level off, at least temporarily before proceeding with an increasingly upward trend or a downward trend. In the displacement plot 930, this is representative of the displacement curve inflection point (filled circles) and indicated by the solid vertical lines for RVA, GCV and LB (MA times). FIG. 9 also indicates that the MA times are as follows: RVA<GCV<LB. In the plot 930, a slight dip occurs for the LB displacement curve prior to leveling off. To avoid marking a MA time by such a slight dip, an algorithm can determine if a rate of change in displacement after a minimum or maximum (e.g., depending on whether displacement is expected to increase or decrease) is less than a predetermined value. For example, in the plot 930, while actual times in milliseconds are not shown, the trial data indicates that the dip or minimum occurs at about 1700 ms and a plateau occurs in the LB displacement at about 1770 ms and the plateau spans about 100 ms. An algorithm may be programmed to account for particularities of a region of the heart based on a priori knowledge (e.g., knowing that the mechanical activation times occur in a particular order or that a region may exhibit particular displacement morphology).

Figure 10:
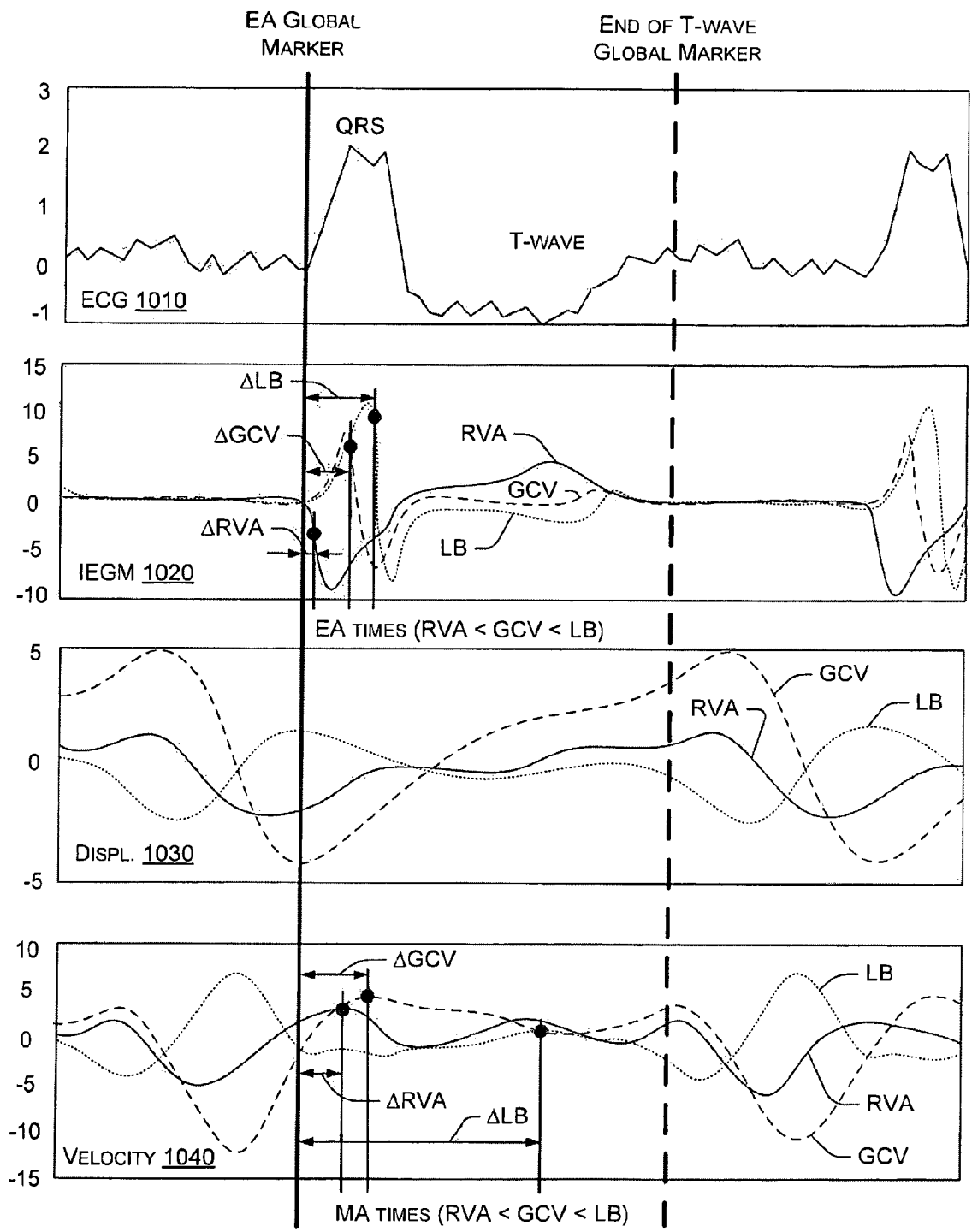
FIG. 10 is a series of plots for electromechanical information where markers indicate various aspects of electrical activity (e.g., IEGM) and mechanical activity (e.g., velocity).

FIG. 10 shows a series of plots including an ECG plot 1010, an IEGM plot 1020, a displacement plot 1030 and a velocity plot 1040. The trial data of FIG. 10 was acquired based on spontaneous rhythms (e.g., intrinsic). Arrangements included electrode-bearing leads positioned in the RV apex (RVA, solid curve), Great Cardiac Vein (GCV, dashed curve), and Lateral Branch (LB, dotted curve). The ECG plot 1010 data was acquired using surface electrodes and the IEGM plot 1020 data was acquired using unipolar sensing. The data of the plots 1010, 1020, 1030 and 1040 is the same as the plots of FIG. 9. However, where the displacement plot 930 of FIG. 9 illustrates a manner to determine mechanical activation times, in FIG. 10, the velocity plot 1040 illustrates an alternative manner to determine mechanical activation times (MA times).

In the approach of FIG. 10, mechanical activation may be taken to be the point of maximal instantaneous change in position, that is, where $$v_i = \frac{|x_i - x_{i-1}|}{t_i - t_{i-1}}$$

reaches a maximum over all points i in a single cardiac cycle. This is representative of the time to peak velocity, and is illustrated in the velocity versus time plot 1040 of FIG. 10.

In another approach, a pseudo-velocity can be computed by $$v'_i = \frac{|s_i - s_{i-1}|}{t_i - t_{i-1}},$$

which is representative of the rate of change of distance from the location at electrical activation; mechanical activation could also be taken as this maximum. Similarly, mechanical activation could be taken as the time to peak acceleration, that is, the second time derivative of the position signal, or other key points in the mechanical cycle. Additionally, the mechanical activation point may be determined as the time when the displacement, velocity, or acceleration reaches a predetermined threshold value, not necessarily a peak. For example a "take-off" point of displacement can be determined when the electrode achieves a certain speed; motion occurring at less than this speed can be considered part of a baseline for cardiac motion. In yet another alternative, a mechanical activation point may be determined as the time when the velocity approaches zero or when the change in position is below a certain small value; in this approach, the point represents commencement of a "pause" between systolic and diastolic phases of the cardiac cycle. Hence, a change in position below a certain small value can be a subthreshold amplitude of position change at consecutive sample points and correspond to a physiologic pause in a cardiac cycle.

As described herein, with reference to the plots of FIGS. 9 and 10, local electromechanical delay (LEMD) can be computed as the time from local electrical activation (EA time) based on a local IEGM (e.g., the three vertical lines in the plots 920 and 1020) to time of local mechanical activation (MA time) based on a displacement or velocity motion signal (e.g., the three vertical lines in the plots 930 and 1040). FIGS. 9 and 10, it is clear that lateral branch (LB) has the largest electromechanical delay and could be selected as an appropriate location for placement of a LV lead for CRT or other LV pacing therapy.

As the electromechanical delay can be computed for each electrode in each configuration, a collection of LEMDs associated with the anatomic location at which each is measured can be used to determine a regional or global electromechanical index. For example, by using interpolation to estimate electromechanical delay between electrodes, a color-coded map can be projected onto a representation of the heart surface to distinguish areas of short electromechanical delay in one color from areas of longer electromechanical delay in another color. Such a map can help a clinician delineate healthy and ischemic zones, as stunned or ischemic myocardium can be expected to have longer electromechanical delay. Other disease processes also affect excitation-contraction coupling to an extent that such an electromechanical dissociation map could indicate affected regions of the heart. Knowledge of where these regions are in respect to a number of possible electrode positions can help guide the final lead placement (e.g., in an intraoperative process).

In an alternative approach, a global electromechanical dissociation index can be computed, without the need for a map, for example, by taking the mean, median, standard deviation, or average deviation of all measured LEMDs from recorded electrodes. In this approach, the index resulting from various configurations can be compared, and the configuration yielding the best value for the index may be selected as an optimal configuration for delivery of a cardiac pacing therapy.

An exemplary technique can analyze information to represent behavior of a "piece" of myocardium. For example, two or more electrodes that are near to one another can represent a piece of myocardium. In this example, electrical activation may be determined by acquiring a bipolar electrogram between a pair of electrodes. Local shortening can be computed as the amplitude of the vector difference between the pair. Further, in this example, LEMD can be computed as the time delay between the time of electrical activation and the time of peak shortening or peak shortening velocity.

For various analyses (e.g., an electromechanical dissociation map, global electromechanical delay standard deviation, using time to peak displacement or velocity for the mechanical activation), the electromechanical interval is a relative period of time. That is, independent of when in the cardiac cycle a region of tissue is activated, the electromechanical delay is triggered off local electrical activation. A set of analogous measures can also be computed by instead using a global trigger.

In various examples, a signal such as a surface QRS, a pre-specified early-activating EGM, or another biosignal may be used to determine a baseline time $t_o$ that can be used for all electrodes. In such scenarios, the electrical delay can be defined as the time from a global trigger to a local EGM activation and the mechanical delay can be defined as the time from the global trigger to local mechanical activation.

FIG. 11 shows a series of plots including an ECG plot 1110, a displacement plot 1130 and a velocity plot 1140. The trial data of FIG. 11 was acquired based on spontaneous rhythms (e.g., intrinsic). Arrangements included electrode-bearing leads positioned in the RV apex (RVA, solid curve), Great Cardiac Vein (GCV, dashed curve), and Lateral Branch (LB, dotted curve). The ECG plot 1110 data was acquired using surface electrodes. The data of the plots 1110, 1130 and 1140 is the same as the plots of FIGS. 9 and 10.

The plots 1110 and 1130 of FIG. 11 illustrate how peak displacement may indicate mechanical activation time. In the example of FIG. 11, "mechanical delay" refers specifically to the time of Q-wave onset in a surface ECG to onset of motion (e.g., typically reported as "electromechanical delay" in echocardiography). Using this approach, the local electromechanical delay can be determined as the difference between the time of local electrical activation and the time of local mechanical activation (MA time), which is still a relative number. However, information regarding at what point in the cardiac cycle each electrode achieves activation is retained.

With respect to a global index, such an index can include both local electromechanical delay (EMD) and local electrical latency (LAT): $GI=\Phi(\alpha 19\ EMD+\beta \cdot LAT)$, where $\Phi$ is an aggregate function such as mean or standard deviation, and $\alpha$ and $\beta$ are weighting coefficients. This approach accounts for the postulate that by more quickly and uniformly activating the entire ventricle, pump function can be improved. Again, this global index could be represented in a summary number to be compared across interventions, or the aggregate of local values could be projected onto an anatomic map to guide lead placement.

In the approaches discussed with respect to FIGS. 9, 10 and 11 motion of a single electrode was used to determine a time point for mechanical activation. In various approaches that follow, motions of more than one electrode can be used to determine a time point for mechanical activation.

An exemplary approach specifies one or more electrodes to represent motion of a region of the heart. For example, for a quadpolar lead in a lateral branch of the coronary sinus, a distal electrode may represent the apical-lateral segment of the heart, the middle two electrodes may represent the mid-lateral segment of the heart, and a proximal electrode may represent the basal-lateral segment of the heart. According to this example, motions of all electrodes in a specified region can be averaged to determine an overall segmental motion. By finding the time of electrical activation as already described, and by finding the time of mechanical activation of this derived segment, a regional electromechanical delay can be computed.

Another exemplary approach specifies two or more electrodes to represent an axis of the heart. For example, an RV electrode can be selected to represent a septal position, while a coronary sinus electrode in a lateral branch can be selected to represent a lateral "freewall" position. A straight line connecting these two electrodes approximates a short axis of the heart.

Similarly, a first electrode at the ostium of the coronary sinus or at the takeoff of a branch from the coronary sinus (e.g., a tributary to the coronary sinus), and a second electrode very distal in a coronary sinus branch, may be selected to approximate a long axis of the left ventricle. The line between any two electrodes can be computed as the vector difference of their positions, and the length of the vector can represent the length of a cardiac axis.

With respect to mechanical activation for an axis, such a time can be defined as the time point when the axis length is at its shortest (e.g., end systole) or as the time point when the rate of change of axis length is largest negative (e.g., peak shortening velocity). Electrical triggering can preferably be taken from a surface ECG (e.g., during implant) or from the first deflection of a far-field ventricular electrogram (e.g., using a unipolar atrial sensing configuration). Accordingly, electromechanical delay can be computed as the time from a Q-wave of the ECG or an atrial IEGM-far-field earliest deflection to time of peak shortening velocity or to time of end systolic length. This number represents a global activation time, and the configuration amongst others yielding the shortest delay can be considered the best configuration.

As noted, the time from onset of a Q-wave (measured per an ECG) or from earliest deflection of far-field ventricular potential to the time of motion onset may be considered equivalent to the echocardiography description of "electromechanical delay" This particular parameter is indicative of isovolumic contraction time ($T_{IVC}$): myocardium is activated but has not yet begun to eject blood from the chamber. In like manner, the isovolumic relaxation time ($T_{IVR}$) can be described as the time from T-wave detection, T-wave peak, or T-wave end, to the time of onset of motion during diastole.

Figure 12:
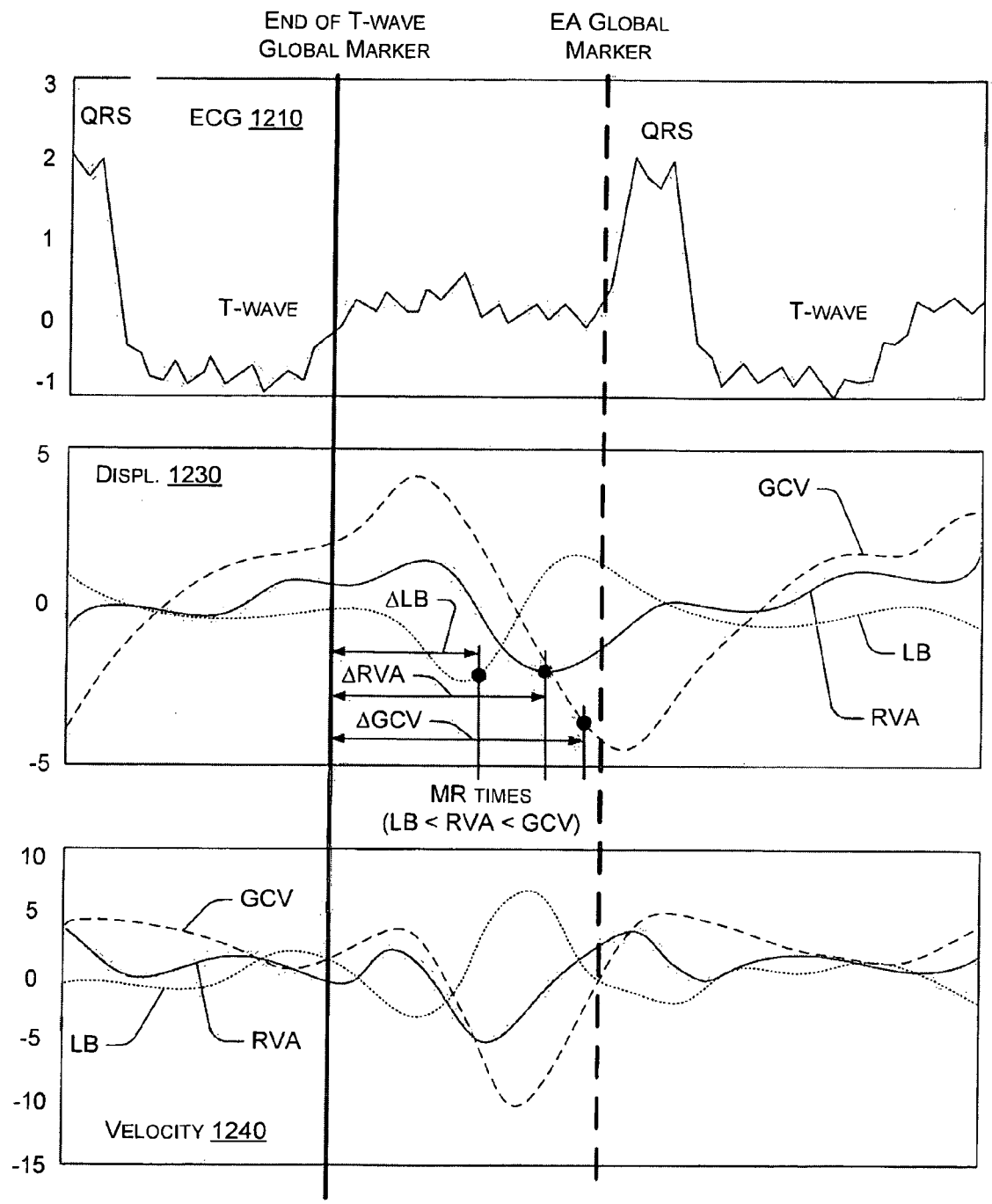
FIG. 12 is a series of plots for electromechanical information where markers indicate various aspects of mechanical activity (e.g., displacement).

FIG. 12 shows a series of plots including an ECG plot 1210, a displacement plot 1230 and a velocity plot 1240. The trial data of FIG. 12 was acquired based on spontaneous rhythms (e.g., intrinsic). Arrangements included electrode-bearing leads positioned in the RV apex (RVA, solid curve), Great Cardiac Vein (GCV, dashed curve), and Lateral Branch (LB, dotted curve). The ECG plot 1210 data was acquired using surface electrodes. The data of the plots 1210, 1230 and 1240 differs in time from the data of the plots of FIGS. 9, 10 and 11. Specifically, the time frame is shifted where a global marker (solid vertical line extending across plots) corresponds to end of a T-wave and another global marker (dashed vertical line extending across plots) corresponds to the onset of a following Q-wave (e.g., QRS complex). In the example of FIG. 12, local mechanical relaxation time interval (LMRTI) is defined as the time from end of a T-wave (global) to minimum diastolic distance (vertical lines in the displacement plot 1230), which is referred to as a mechanical relaxation time or time of mechanical relaxation (MR time).

According to the approach of FIG. 12, the end of a T-wave is a feature for electrical reference and a peak negative diastolic displacement is a feature for mechanical reference where the time difference between these two references is the mechanical relaxation time interval (MRTI). Ejection time ($T_{Ej}$) can be defined as the time after isovolumic contraction (IVC) and before isovolumic relaxation (IVR). Total filling time ($T_{TF}$) can be defined as the time after IVR and before IVC. This interval can be further subdivided into passive, or early, filling ($T_{EF}$), which can be estimated as the time from IVR to the onset of motion of an atrial electrode, and late, or active filling ($T_{AF}$), the time from onset of motion of an atrial electrode to the beginning of IVR. These intervals can be considered as analogous to echo measures of IVC, IVR, ejection, early and active filling; in echo, these are typically delineated by visualization of the mitral and aortic valves opening and closing and/or by Doppler flow traces across the mitral and aortic annuli.

As described herein, knowledge of timing intervals of the cardiac cycle enables computation of analogues to other echocardiographic parameters, such as the Tei Index (($T_{IVC}+T_{IVR})/T_{Ej}$), for example. By varying pacing parameters such as electrode location, electrode polarity, and inter-chamber delays, a clinician responsible for implanting or otherwise setting-up an implantable device can program a pacing therapy to achieve an indicated best value of timing indices, for example, to minimize the Tei index.

When used in conjunction with other hemodynamic data, such as cardiogenic impedance measured from the intracardiac leads, the time delineation of the cardiac cycle can be used to piece together pressure-volume-loop-like traces, which, in turn, provide insight into global function. In particular, a clinician may program AV delay to thereby vary cardiac preload and then use a locating system such as the ENSITE® NavX system to track motion. Based on such information, the clinician may find the time of isovolumic relaxation while simultaneously noting an impedance vector that relates to the left ventricle whereby an estimate of end-systolic elastance or contractility can be ascertained. By subsequently pacing from different locations or configurations, a pacing therapy yielding the best contractility may be found.

As described herein, various exemplary methods, devices, systems, etc., can help optimize CRT or other pacing therapy by using one or more electromechanical delay related parameters. An electromechanical delay may be determined based on combining an intracardiac electrogram with electrode motion as tracked by a locating system (e.g., the ENSITE® NavX system).

Electrode locating technology can be used not only to locate electrodes for the creation of electroanatomic maps, but also to track the real-time motion of electrodes in three dimensions. Tracking electrodes in the intracardiac, intravascular, or intrapericardial space over the course of one or more cardiac cycles can provide an estimate of myocardial motion. Such motions, and specifically the timing of these motions, can be used to derive electromechanical delay parameters that estimate cardiac performance during or after implantation of a device configured to deliver CRT or other cardiac pacing therapy. Such parameters can be used to optimize pacing lead location, electrode configuration, and/or interelectrode timing.

While various examples pertain to local measures, by aggregation of electrogram data at multiple locations on the heart, an estimate of global dispersion of electrical activation can be made. Similarly, from the aggregation of motion data at multiple locations on the heart, an estimate of global dispersion of mechanical activation can be made. Further, by combining the electrical and mechanical data for a single location, the local electromechanical properties such as electromechanical dissociation or electromechanical delay can be determined. Acute global electrical and mechanical properties can represent an estimate of whether and to what degree an intervention such as CRT will be successful (e.g., likelihood of responding to CRT), while local electromechanical properties can be used to determine myocardial viability and to identify favorable areas to pace for improvement of chamber synchrony or locations to avoid pacing because of vulnerability to arrhythmogenesis.

As mentioned, motion information may be influenced by respiration. For example, respiratory sinus arrhythmia (RSA) causes an increase in heart rate during inspiration due to inhibition of parasympathetic nerve transmission and/or firing, which shifts autonomic tone or balance toward parasympathetic. While during expiration, heart rate decreases as parasympathetic nerve transmission and/or firing resumes.

Motion information may also be affected by motion due to respiration. For example, intrathoracic pressure varies between inspiration and expiration, which can affect pericardial pressure. In turn, changes in pericardial pressure can affect motion of the myocardium. In addition, the thoracic cavity expands and contracts during respiration, which can cause the heart to shift position. Hence, respiration can alter motion information via cardiopulmonary effects, autonomic effects, pressure effects, position effects, etc.

In general, during rest, a respiratory cycle may last about 6 seconds and therefore encompass about 6 or more cardiac cycles. During a respiratory cycle, the heart typically translates, accordingly, an exemplary method may measure such motion and compensate appropriately to uncover motion due primarily to cardiac mechanics. As described herein, a chest band, a mouthpiece, an impedance signal, etc., may be used to monitor respiration. Alternatively, or in addition to, an intrinsic heart rate may be used to monitor respiration where the heart rate reflects respiratory sinus arrhythmia.

Where desired, a method may acquire cardiac motion information for a cardiac cycle at or near peak inspiration and at a cardiac cycle at or near peak expiration. A comparison between cardiac motion information for these two states may provide insight into cardiac mechanics.

An exemplary method includes providing a mechanical activation time (MA time) for a myocardial location, the location defined at least in part by an electrode and the mechanical activation time determined at least in part by movement of the electrode; providing an electrical activation time (EA time) for the myocardial location where the electrical activation time is a time determined by electrical cardiac activity data acquired using the electrode over at least a portion of a cardiac cycle; and determining an electromechanical delay (EMD) for the myocardial location based on a difference between the mechanical activation time (MA time) and the electrical activation time (EA time). Such a method may include analysis of acquired information such as the information shown in FIGS. 9-12, which show collectively various times (e.g., MA times, EA times, etc.).

In the foregoing method, the mechanical activation time can be a time determined based on position data for the electrode where the electrode measures potential in a current field (e.g., using a localization system such as the ENSITE® system). In various examples, a mechanical activation time and an electrical activation time are provided based on information acquired during a single cardiac cycle. Alternatively, these times may be based on information acquired during multiple cardiac cycles. Further, in either instance, electrical information may be acquired at a first sampling rate and mechanical information may be acquired at a second sampling rate. Specifics of equipment or various concerns may determine how to set sampling rates. In some instances, electrical information may be acquired for a cardiac cycle and mechanical information acquired for a subsequent cardiac cycle or vice versa.

As described herein, an exemplary method may include selecting one or more parameters for delivery of cardiac pacing therapy based at least in part on a determined electromechanical delay. For example, one or more parameters may include at least one parameter selected from a group consisting of electrode location, electrode polarity, number of electrodes, timing of stimulation, delay between delivery of stimuli, stimulation energy, stimulation duration, and stimulation polarity. Various methods are suitable for use with a variety of cardiac pacing therapies, including bi-ventricular cardiac pacing therapies (e.g., CRT or other).

As described herein, an exemplary method may include diagnosing a cardiac condition based at least in part on a determined electromechanical delay. For example, a cardiac condition may be a condition selected from a group consisting of ischemia, tissue viability, scarring, arrhythmogenesis, dyssynchrony, myopathy and congestive heart failure.

As discussed, various techniques can be implemented to determine a mechanical activation time (MA time). For example, it may be determined at a peak amplitude or a threshold amplitude of a displacement vector, representing instantaneous location of the electrode, with reference to location of the electrode at the electrical activation time (EA time). In another example, a mechanical activation (MA time) is determined at a peak amplitude or a threshold amplitude of instantaneous velocity of the electrode, the instantaneous velocity derived from instantaneous location of the electrode at consecutive sample points in time. In yet another example, a mechanical activation (MA time) is determined at a peak amplitude or a threshold amplitude of a rate of change of distance of instantaneous location of the electrode, with reference to the location of the electrode at the electrical activation time (EA time). In another example, a mechanical activation (MA time) is determined at a zero instantaneous velocity or a sub-threshold amplitude of position change at consecutive sample points, corresponding to a physiologic pause in a cardiac cycle. Such examples may be understood better with respect to the information presented in FIGS. 9-12. Specifically, any of a variety of techniques pertaining to amplitudes, derivatives, etc., may be understood better in view of the plots of FIGS. 9-12.

As described herein, an exemplary method can include determination of an electromechanical delay by triggering acquisition of mechanical information using an electrode based at least in part on detection of an electrical activation time (EA time) local to the electrode where the information is sufficient to determine the mechanical activation time (MA time).

An exemplary method may include determining mechanical latency as a time interval from a time of onset of a Q-wave in a surface ECG (global EA time) to a time of mechanical activation (MA time), determining electrical latency as a time interval from a time of onset of a Q-wave in a surface ECG to a time of local electrical activation (local EA time) in a IEGM, and determining the electromechanical delay (EMD) as a difference between the determined mechanical latency and the determined electrical latency. Such an approach may be appreciated by reference to FIGS. 9 and 10, which show ECGs and IEGMs.

An exemplary method can include determining mechanical latency as a time interval from a time of first deflection of an intracardiac far-field ventricular potential to a time of mechanical activation (MA time), determining a local electrical latency as a time interval from a time of first deflection of an intracardiac far-field ventricular potential to a time of electrical activation (EA time) in an IEGM, and determining the electromechanical delay (EMD) as a difference between the determined mechanical latency and the determined electrical latency. Such a method may appropriately rely on an electrode configuration suited to sense far-field ventricular signals. Various techniques for sensing far-field ventricular signals and detecting ventricular events may be implemented using a device such as the device 100 of FIGS. 1 and 2. In general, far-field refers to signals sensed using one or more implanted electrodes (e.g., as opposed to surface ECG acquisition techniques).

As described herein, an exemplary method can include determining a local electromechanical delay for each of a plurality of implanted electrodes. Further, as discussed with respect to FIG. 3 (see, e.g., block 340), various exemplary methods can include determining one or more regional EMDs and/or one or more global EMDs. In general, a system that includes various features of the system 1300 of shown in FIG. 13 can provide for presenting graphically one or more electromechanical delays along with respective anatomic locations, mapped on an image of the heart, to thereby yield a map tool to guide CRT lead placement.

As described herein, a system may include one or more statistical analysis algorithms or modules. For example, given such capabilities, a method may include aggregating individually determined electromechanical delays from a plurality of implanted electrodes and determining statistics for the electromechanical delays to provide a global electromechanical delay index.

An exemplary method may include determining an electromechanical delay based on recorded cardiac electrograms and recorded positions of one or more electrodes with respect to time during one or more cardiac cycles, where the recorded positions are recorded positions for respective locations of one or more electrode where the respective locations are due to maneuvering of the one or more electrodes within a cardiac space. Such a method may also include generating an electromechanical delay map or index after recording positions for two or more locations.

In another exemplary method, an electromechanical delay can be determined based on recorded cardiac electrograms and recorded positions of one or more electrodes with respect to time during one or more cardiac cycles, where the recorded positions are recorded positions taken at various fixed locations as one or more additional electrodes are maneuvered within the cardiac space. In this approach, a method may include providing pacing at different locations and generating a separate electromechanical index or map for each respective pacing location.

As EMDs may be regional (see, e.g., block 340 of FIG. 3), a method may include defining a region by specific locations of each of a plurality of electrodes in a cardiac space and determining an electromechanical delay for the region. As EMDs may be global (see, e.g., block 340 of FIG. 3), a method may include defining a representative vector or cardiac axis by specific locations of each of a plurality of electrodes in a cardiac space and defining a global mechanical latency as a time interval from an electrical activity time trigger to a time of minimum vector or axis length or peak vector or axis shortening velocity.

As described herein, in various methods, onset of motion of an electrode, after detection of a T-wave, can indicate beginning of diastolic relaxation and/or onset of motion of an electrode located in the right atrium can indicate beginning of active diastolic filling. More generally, times of onset of motion of various electrodes, with respect to associated cardiac electrograms, can delineate phases of a cardiac cycle. Given such phases, an exemplary method may include determining indices of global cardiac function based in part on durations of the various phases of a cardiac cycle.

As described herein, an exemplary system can include one or more processors; memory; and control logic, implemented at least in part by the one or more processors and the memory, configured to: determine a mechanical activation time (MA time) for a myocardial location, the location defined at least in part by an electrode and the mechanical activation time (MA time) determined at least in part by movement of the electrode; determine an electrical activation time (EA time) for the myocardial location where the electrical activation time (EA time) is a time determined by electrical cardiac activity data acquired using the electrode over at least a portion of a cardiac cycle; and determine an electromechanical delay (EMD) for the myocardial location based on a difference between the mechanical activation time (MA time) and the electrical activation time (EA time).

Exemplary External Programmer

Figure 13:
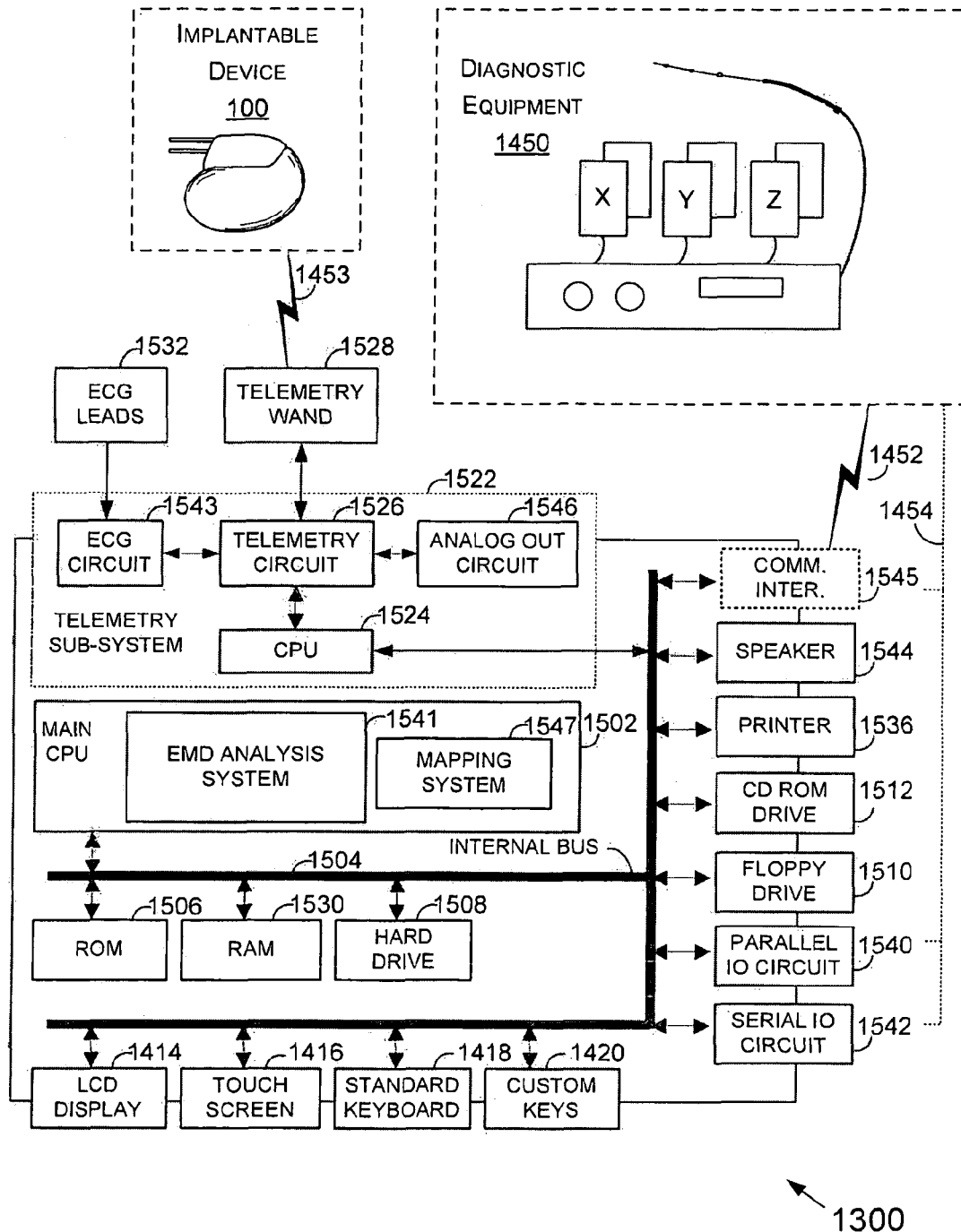
FIG. 13 is an exemplary system for acquiring information and analyzing such information.

FIG. 13 illustrates pertinent components of an external programmer 1300 for use in programming an implantable medical device 100 (see, e.g., FIGS. 1 and 2). The external programmer 1300 optionally receives information from other diagnostic equipment 1450, which may be a computing device capable of acquiring motion information related to cardiac mechanics. For example, the equipment 1450 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1300 in distinguishing respiratory motion from cardiac.

Briefly, the programmer 1300 permits a clinician or other user to program the operation of the implanted device 100 and to retrieve and display information received from the implanted device 100 such as IEGM data and device diagnostic data. Where the device 100 includes a module such as the motion module 239, then the programmer 1300 may instruct the device 100 to measure potentials and to communicate measured potentials to the programmer via a communication link 1453. The programmer 1300 may also instruct a device or diagnostic equipment to deliver current to generate one or more potential fields within a patient's body where the implantable device 100 may be capable of measuring potentials associated with the field(s).

The external programmer 1300 may be configured to receive and display ECG data from separate external ECG leads 1532 that may be attached to the patient. The programmer 1300 optionally receives ECG information from an ECG unit external to the programmer 1300. As already mentioned, the programmer 1300 may use techniques to account for respiration.

Depending upon the specific programming, the external programmer 1300 may also be capable of processing and analyzing data received from the implanted device 100 and from ECG leads 1532 to, for example, render diagnosis as to medical conditions of the patient or to the operations of the implanted device 100. As noted, the programmer 1300 is also configured to receive data representative of conduction time delays from the atria to the ventricles and to determine, therefrom, an optimal or preferred location for pacing. Further, the programmer 1300 may receive information such as ECG information, IEGM information, information from diagnostic equipment, etc., and determine one or more electromechanical delay (e.g., consider the method 300 and the method 700).

Now, considering the components of programmer 1300, operations of the programmer are controlled by a CPU 1502, which may be a generally programmable microprocessor or microcontroller or may be a dedicated processing device such as an application specific integrated circuit (ASIC) or the like. Software instructions to be performed by the CPU are accessed via an internal bus 1504 from a read only memory (ROM) 1506 and random access memory 1530. Additional software may be accessed from a hard drive 1508, floppy drive 1510, and CD ROM drive 1512, or other suitable permanent or removable mass storage device. Depending upon the specific implementation, a basic input output system (BIOS) is retrieved from the ROM 1506 by CPU 1502 at power up. Based upon instructions provided in the BIOS, the CPU 1502 "boots up" the overall system in accordance with well-established computer processing techniques.

Once operating, the CPU 1502 displays a menu of programming options to the user via an LCD display 1414 or other suitable computer display device. To this end, the CPU 1502 may, for example, display a menu of specific programming parameters of the implanted device 100 to be programmed or may display a menu of types of diagnostic data to be retrieved and displayed. In response thereto, the clinician enters various commands via either a touch screen 1416 overlaid on the LCD display or through a standard keyboard 1418 supplemented by additional custom keys 1420, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of the optimal pacing location, CPU 1502 includes an electromechanical delay (EMD) analysis system 1541 and a 3-D mapping system 1547. The systems 1541 and 1547 may receive mechanical information and electrical information from the implantable device 100 and/or diagnostic equipment 1450. The EMD system 1541 optionally includes control logic to associate information and to make one or more conclusions based on an EMD or EMDs (e.g., consider the LEMDs, REMDs and GEMDs of block 340 and the conclusions of block 350 of FIG. 3). As shown in FIG. 13, control logic associated with one or more components or modules may be, in part, in the form of processor-executable instructions embodied in one or more processor-readable media (e.g., consider a computer-readable medium such as a storage medium that may be read into memory). Hence, the CPU 1502 or the CPU 1524 may implement control logic. Control logic may be in the form of circuitry, instructions or a combination of circuitry and instructions. Various methods described herein may be implemented, at least in part, by control logic (e.g., in a system such as the system 1300).

Where information is received from the implanted device 100, a telemetry wand 1528 may be used. Other forms of wireless communication exist as well as forms of communication where the body is used as a "wire" to communicate information from the implantable device 100 to the programmer 1400.

If information is received directly from diagnostic equipment 1450, any appropriate input may be used, such as parallel IO circuit 1540 or serial IO circuit 1542. Motion information received via the device 100 or via other diagnostic equipment 1450 may be analyzed using the mapping system 1547. In particular, the mapping system 1547 (e.g., control logic) may identify positions within the body of a patient and associate such positions with one or more electrodes where such electrodes may be capable of delivering stimulation energy to the heart.

A communication interface 1545 optionally allows for wired or wireless communication with diagnostic equipment 1450 or other equipment. The communication interface 1545 may be a network interface connected to a network (e.g., intranet, Internet, etc.).

A map or model of cardiac motion may be displayed using display 1414 based, in part, on 3-D heart information and optionally 3-D torso information that facilitates interpretation of motion information. Such 3-D information may be input via ports 1540, 1542, 1545 from, for example, a database, a 3-D imaging system, a 3-D location digitizing apparatus (e.g., stereotactic localization system with sensors and/or probes) capable of digitizing the 3-D location. According to such an example, a clinician can thereby view the optimal location for delivery of stimulation energy on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1300 optionally records procedures and allows for playback (e.g., for subsequent review). For example, a heart map and all of the electrical activation data, mechanical activation data, EMD data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1522 may include its own separate CPU 1524 for coordinating the operations of the telemetry subsystem. In a dual CPU system, the main CPU 1502 of programmer communicates with telemetry subsystem CPU 1524 via internal bus 1504. Telemetry subsystem additionally includes a telemetry circuit 1526 connected to telemetry wand 1528, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1300 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1300 (e.g., within a random access memory (RAM) 1530, hard drive 1508, within a floppy diskette placed within floppy drive 1510). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1300 has a communication link to an external storage device or network storage device, then information may be stored in such a manner (e.g., on-site database, off-site database, etc.). The programmer 1300 optionally receives data from such storage devices.

A typical procedure may include transferring all patient and device diagnostic data stored in an implanted device 100 to the programmer 1300. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1522 receives ECG signals from ECG leads 1532 via an ECG processing circuit 1534. As with data retrieved from the implanted device 100, signals received from the ECG leads are stored within one or more of the storage devices of the programmer 1300. Typically, ECG leads output analog electrical signals representative of the ECG. Accordingly, ECG circuit 1534 includes analog to digital conversion circuitry for converting the signals to digital data appropriate for further processing within programmer 1600. Depending upon the implementation, the ECG circuit 1543 may be configured to convert the analog signals into event record data for ease of processing along with the event record data retrieved from the implanted device. Typically, signals received from the ECG leads 1532 are received and processed in real time.

Thus, the programmer 1300 is configured to receive data from a variety of sources such as, but not limited to, the implanted device 100, the diagnostic equipment 1450 and directly or indirectly via external ECG leads (e.g., subsystem 1522 or external ECG system). The diagnostic equipment 1450 includes wired 1454 and/or wireless capabilities 1452 which optionally operate via a network that includes the programmer 1300 and the diagnostic equipment 1550 or data storage associated with the diagnostic equipment 1450.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1502, the programming commands are converted to specific programming parameters for transmission to the implanted device 100 via telemetry wand 1528 to thereby reprogram the implanted device 100 or other devices, as appropriate.

Prior to reprogramming specific parameters, the clinician may control the external programmer 1300 to display any or all of the data retrieved from the implanted device 100, from the ECG leads 1532, including displays of ECGs, IEGMs, statistical patient information (e.g., via a database or other source), diagnostic equipment 1450, etc. Any or all of the information displayed by programmer may also be printed using a printer 1536.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1300 optionally includes a modem to permit direct transmission of data to other programmers via the public switched telephone network (PSTN) or other interconnection line, such as a T1 line or fiber optic cable. Depending upon the implementation, the modem may be connected directly to internal bus 1504 may be connected to the internal bus via either a parallel port 1540 or a serial port 1542.

Other peripheral devices may be connected to the external programmer via the parallel port 1540, the serial port 1542, the communication interface 1545, etc. Although one of each is shown, a plurality of input output (IO) ports might be provided. A speaker 1544 is included for providing audible tones to the user, such as a warning beep in the event improper input is provided by the clinician. Telemetry subsystem 1522 additionally includes an analog output circuit 1546 for controlling the transmission of analog output signals, such as IEGM signals output to an ECG machine or chart recorder.

With the programmer 1300 configured as shown, a clinician or other user operating the external programmer is capable of retrieving, processing and displaying a wide range of information received from the ECG leads 1532, from the implanted device 100, the diagnostic equipment 1450, etc., and to reprogram the implanted device 100 or other implanted devices if needed. The descriptions provided herein with respect to FIG. 13 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
providing a mechanical activation time (MA time) for a myocardial location, the location defined at least in part by an electrode, and the mechanical activation time determined at least in part by movement of the electrode, wherein the mechanical activation time comprises a time determined based on position data for the electrode wherein the electrode measures potential in a current field;
providing an electrical activation time (EA time) for the myocardial location wherein the electrical activation time comprises a time determined by electrical cardiac activity data acquired using the electrode over at least a portion of a cardiac cycle; and
determining an electromechanical delay (EMD) for the myocardial location based on a difference between the mechanical activation time (MA time) and the electrical activation time (EA time).

2. The method of claim 1 wherein the mechanical activation time and the electrical activation time are provided based on information acquired during a single cardiac cycle.

3. The method of claim 2 wherein the information comprises electrical information acquired at a first sampling rate and mechanical information acquired at a second sampling rate.

4. The method of claim 1 wherein the mechanical activation time and the electrical activation time are provided based on information acquired during multiple cardiac cycles.

5. The method of claim 4 wherein the information comprises electrical information acquired for a cardiac cycle and mechanical information acquired for a subsequent cardiac cycle or vice versa.

6. The method of claim 1 further comprising selecting one or more parameters for delivery of cardiac pacing therapy based at least in part on the determined electromechanical delay, wherein the one or more parameters are selected from a group consisting of electrode location, electrode polarity, number of electrodes, timing of stimulation, delay between delivery of stimuli, stimulation energy, stimulation duration, and stimulation polarity.

7. The method of claim 1 further comprising diagnosing a cardiac condition based at least in part on the determined electromechanical delay.

8. The method of claim 1 wherein the MA time is determined at a peak amplitude or a threshold amplitude of a displacement vector, representing instantaneous location of the electrode, with reference to location of the electrode at the EA time.

9. The method of claim 1 wherein the MA time is determined at a peak amplitude or a threshold amplitude of instantaneous velocity of the electrode, the instantaneous velocity derived from instantaneous location of the electrode at consecutive sample points in time.

10. The method of claim 1 wherein the MA time is determined at a peak amplitude or a threshold amplitude of a rate of change of distance of instantaneous location of the electrode, with reference to the location of the electrode at the EA time.

11. The method of claim 1 wherein the MA time is determined at a zero instantaneous velocity or a sub-threshold amplitude of position change at consecutive sample points, corresponding to a physiologic pause in a cardiac cycle.

12. The method of claim 1 wherein determination of the electromechanical delay comprises triggering acquisition of mechanical information using the electrode based at least in part on detection of an EA time local to the electrode, the mechanical information sufficient to determine the MA time.

13. The method of claim 1 further comprising determining mechanical latency as a time interval from a time of onset of a Q-wave in a surface ECG (global EA time) to a time of mechanical activation (MA time), determining electrical latency as a time interval from a time of onset of a Q-wave in a surface ECG to a time of local electrical activation (local EA time) in a IEGM, and determining the electromechanical delay (EMD) as a difference between the determined mechanical latency and the determined electrical latency.

14. The method of claim 1 further comprising determining mechanical latency as a time interval from a time of first deflection of an intracardiac far-field ventricular potential to a time of mechanical activation (MA time), determining a local electrical latency as a time interval from a time of first deflection of an intracardiac far-field ventricular potential to a time of electrical activation (EA time) in an IEGM, and determining the electromechanical delay (EMD) as a difference between the determined mechanical latency and the determined electrical latency.

15. The method of claim 1 further comprising determining a local electromechanical delay for each of a plurality of implanted electrodes.

16. The method of claim 15 further comprising presenting graphically each of the electromechanical delays along with respective anatomic locations, mapped on an image of the heart, to thereby yield a map tool to guide CRT lead placement.

17. The method of claim 15 further comprising:
comparing the local electromechanical delays; and
visually or audibly identifying the implanted electrode having the shortest local electromechanical delay as the optimal therapy delivering electrode.

18. The method of claim 1 further comprising aggregating individually determined electromechanical delays from a plurality of implanted electrodes and determining statistics for the electromechanical delays to provide a global electromechanical delay index.

19. The method of claim 1 wherein the electromechanical delay is determined based on recorded cardiac electrograms and recorded positions of one or more electrodes with respect to time during one or more cardiac cycles, wherein the recorded positions comprise recorded positions for respective locations of the one or more electrode, the respective locations due to maneuvering of the one or more electrodes within a cardiac space.

20. The method of claim 19 further comprising generating an electromechanical delay map or index after recording positions for two or more locations.

21. The method of claim 1 wherein the electromechanical delay is determined based on recorded cardiac electrograms and recorded positions of one or more electrodes with respect to time during one or more cardiac cycles, wherein the recorded positions comprise recorded positions taken at various fixed locations as one or more additional electrodes are maneuvered within the cardiac space.

22. The method of claim 21 further comprising providing pacing at different locations and generating a separate electromechanical index or map for each respective pacing location.

23. The method of claim 1 further comprising defining a region by specific locations of each of a plurality of electrodes in a cardiac space and determining an electromechanical delay for the region.

24. The method of claim 1 further comprising defining a representative vector or cardiac axis by specific locations of each of a plurality of electrodes in a cardiac space and defining a global mechanical latency as a time interval from an electrical activity time trigger to a time of minimum vector or axis length or peak vector or axis shortening velocity.

25. The method of claim 1 wherein onset of motion of the electrode, after detection of a T-wave, indicates beginning of diastolic relaxation.

26. The method of claim 1 wherein onset of motion of an electrode located in the right atrium indicates beginning of active diastolic filling.

27. The method of claim 1 wherein times of onset of motion of various electrodes, with respect to associated cardiac electrograms, delineate phases of a cardiac cycle.

28. The method of claim 27 further comprising determining indices of global cardiac function based in part on durations of the various phases of a cardiac cycle.

29. A system comprising:
one or more processors;
memory; and
control logic, implemented at least in part by the one or more processors and the memory, configured to:
 determine a mechanical activation time (MA time) for a myocardial location, the location defined at least in part by an electrode, and the mechanical activation time (MA time) determined at least in part by movement of the electrode, wherein the mechanical activation time comprises a time determined based on position data for the electrode wherein the electrode measures potential in a current field;
 determine an electrical activation time (EA time) for the myocardial location wherein the electrical activation time (EA time) comprises a time determined by electrical cardiac activity data acquired using the electrode over at least a portion of a cardiac cycle; and
 determine an electromechanical delay (EMD) for the myocardial location based on a difference between the mechanical activation time (MA time) and the electrical activation time (EA time).

30. The system of claim 29 further comprising a display, wherein:
the control logic is further configured to determine a local electromechanical delay for each of a plurality of implanted electrodes; and
the display is operative to present graphically each of the electromechanical delays along with respective anatomic locations, mapped on an image of the heart, to thereby yield a map tool to guide CRT lead placement.

31. The system of claim 29 further comprising a user interface, wherein:
the control logic is further configured to determine a local electromechanical delay for each of a plurality of implanted electrodes and compare the local electromechanical delays; and
the user interface is operative to visually or audibly identify the implanted electrode having the shortest local electromechanical delay as the optimal therapy delivering electrode.

* * * * *